(12) United States Patent
Xu

(10) Patent No.: US 10,433,542 B2
(45) Date of Patent: Oct. 8, 2019

(54) ANTIMICROBIAL SUBSTRATE SURFACE

(71) Applicant: IMEC VZW, Leuven (BE)

(72) Inventor: XiuMei Xu, Bertem (BE)

(73) Assignee: IMEC VZW, Leuven (BE)

( * ) Notice: Subject to any disclaimer, the term of this patent is extended or adjusted under 35 U.S.C. 154(b) by 0 days.

(21) Appl. No.: 15/871,190

(22) Filed: Jan. 15, 2018

(65) Prior Publication Data

US 2018/0213772 A1    Aug. 2, 2018

(30) Foreign Application Priority Data

Jan. 31, 2017  (EP) .................................... 17153880
May 9, 2017   (EP) .................................... 17170193

(51) Int. Cl.
| | | |
|---|---|---|
| *A01N 25/10* | (2006.01) | |
| *C08L 53/00* | (2006.01) | |
| *B82B 3/00* | (2006.01) | |
| *A01N 25/34* | (2006.01) | |
| *H01L 21/3065* | (2006.01) | |
| *B81C 1/00* | (2006.01) | |
| *B82Y 30/00* | (2011.01) | |
| *B82Y 40/00* | (2011.01) | |
| *G01N 23/2251* | (2018.01) | |

(52) U.S. Cl.
CPC ............ *A01N 25/10* (2013.01); *A01N 25/34* (2013.01); *B81C 1/00206* (2013.01); *B82B 3/0014* (2013.01); *C08L 53/00* (2013.01); *H01L 21/3065* (2013.01); *B81B 2203/0361* (2013.01); *B81B 2207/056* (2013.01); *B82Y 30/00* (2013.01); *B82Y 40/00* (2013.01); *G01N 23/2251* (2013.01)

(58) Field of Classification Search
None
See application file for complete search history.

(56) References Cited

FOREIGN PATENT DOCUMENTS

WO    WO 2013/154770 A1 * 10/2013 ............. G01N 21/65
WO         2015/031956 A1    3/2015

OTHER PUBLICATIONS

Dickson et al., "Nanopatterned polymer surfaces with bactericidal properties," Biointerphases, Jun. 1, 2015, vol. 10, No. 2, pp. 021010-1 to 021010-8 (Year: 2015).*
Pogodin et al., "Biophysical Model of Bacterial Cell Interactions with Nanopatterned Cicada Wing Surfaces," Biophysical Journal, vol. 104, Feb. 2013, pp. 835-840 (Year: 2013).*
Songmei et al., "Antibacterial Au nanostructured surfaces," Nanoscale, Published Nov. 23, 2015, vol. 8, No. 5, pp. 2620-2625 (Year: 2015).*

(Continued)

*Primary Examiner* — Aradhana Sasan
(74) *Attorney, Agent, or Firm* — McDonnell Boehnen Hulbert & Berghoff LLP

(57) ABSTRACT

Embodiments described herein include an antimicrobial substrate surface. An example embodiment includes a structure that includes an antimicrobial surface on a substrate. The antimicrobial surface includes a plurality of nanostructures. Each nanostructure includes a nanopillar on the substrate. The nanopillar has a height. Each nanostructure also includes a head covering a distal end and at least part of the height of the nanopillar.

19 Claims, 13 Drawing Sheets

(56) References Cited

OTHER PUBLICATIONS

Mueggenburg, Klara E. et al., "Elastic Membranes of Close-Packed Nanoparticle Arrays", Nature Materials, vol. 6, Sep. 2007, pp. 656-660.
Malaquin, Laurent et al., "Controlled Particle Placement through Convective and Capillary Assembly", Langmuir, vol. 23, 2007, pp. 11513-11521.

* cited by examiner

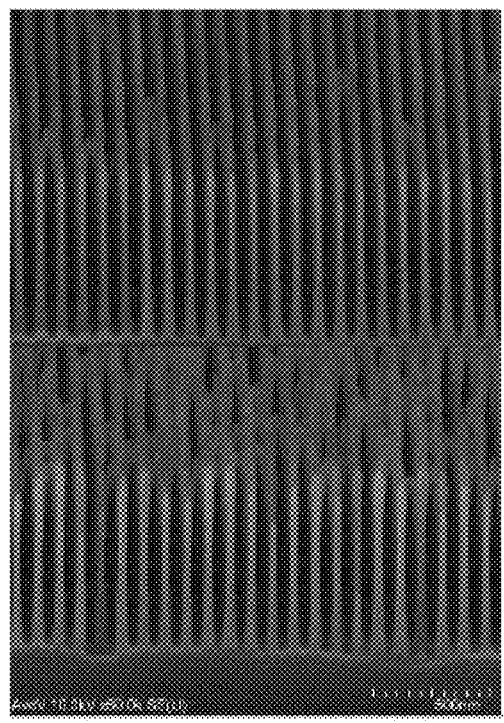 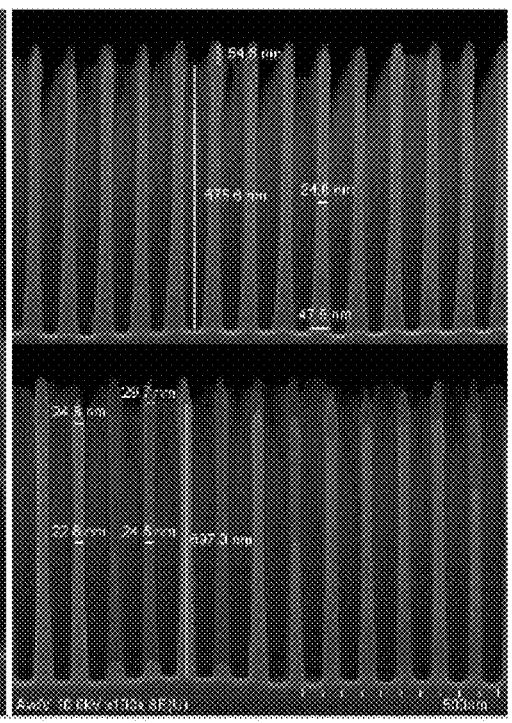
FIG. 6A          FIG. 6B
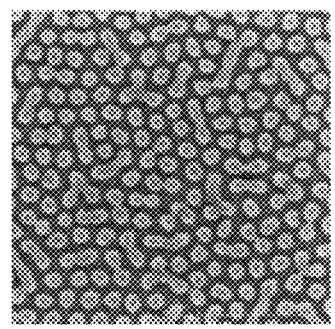 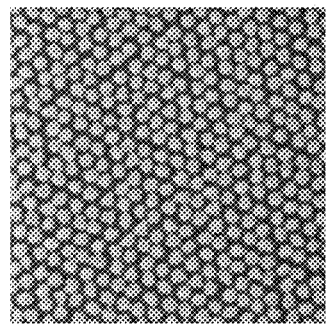
FIG. 7A      FIG. 7B

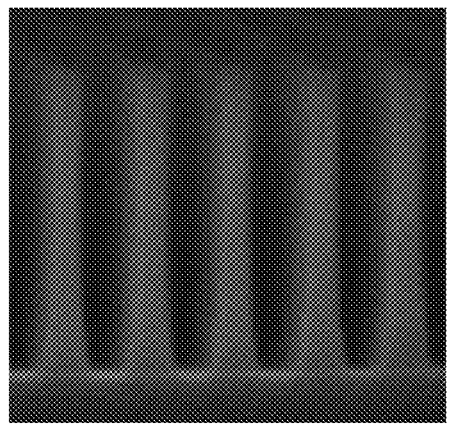
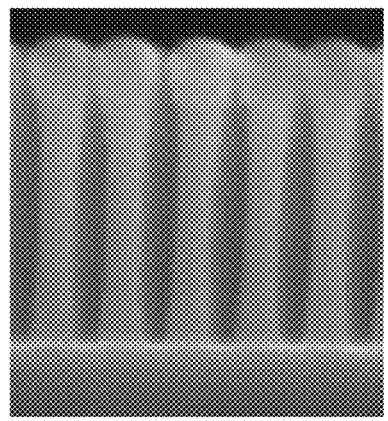
FIG. 16A     FIG. 16B
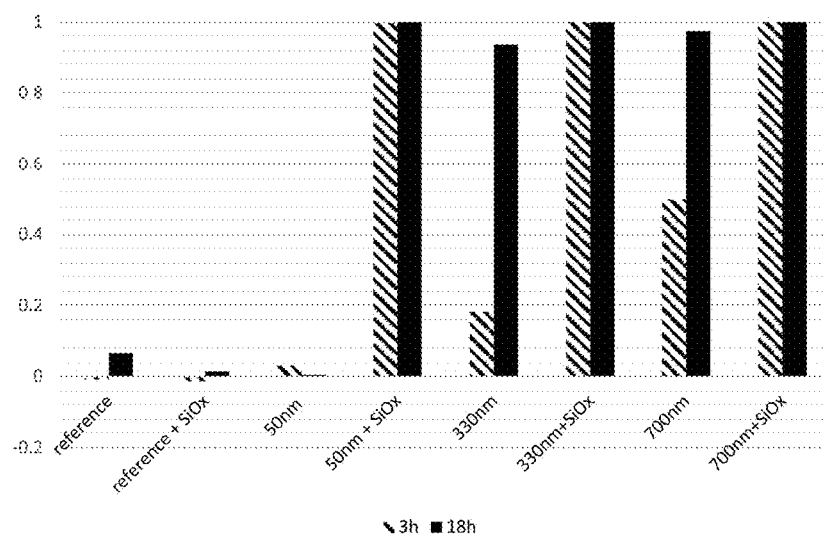
FIG. 17

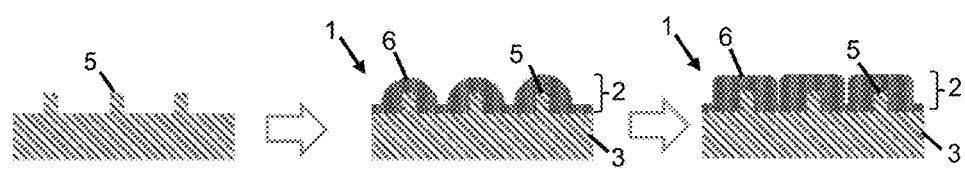
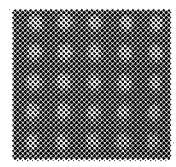 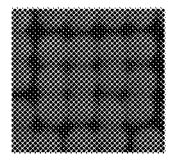 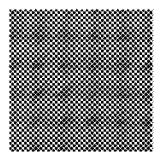
FIG. 18A  FIG. 18B  FIG. 18C
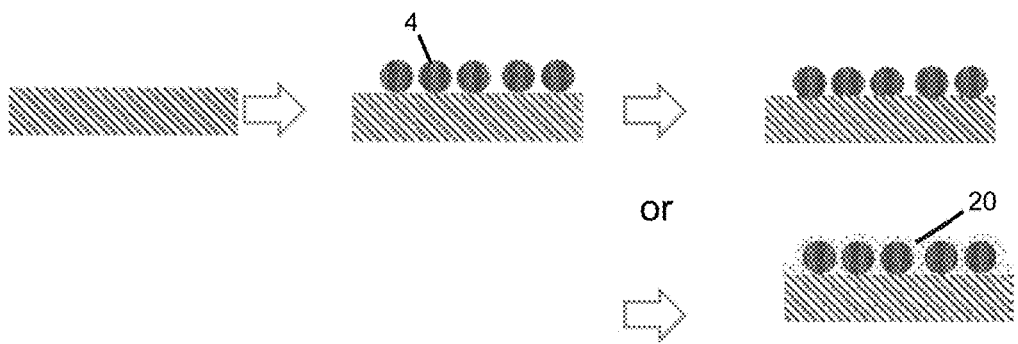
FIG. 19

ANTIMICROBIAL SUBSTRATE SURFACE

CROSS-REFERENCE TO RELATED APPLICATIONS

The present application is a non-provisional patent application claiming priority to European Patent Application No. EP 17170193.1, filed May 9, 2017, and European Patent Application No. EP 17153880.4, filed Jan. 31, 2017; the contents of both applications are hereby incorporated by reference.

FIELD OF THE DISCLOSURE

The present disclosure relates to antimicrobial surfaces and in particular to antimicrobial surfaces comprising a plurality of nanostructures.

BACKGROUND

Most antimicrobial products contain chemically based agents that can kill or slow down the growth of microorganisms, for instance, β-lactams, cephalosporins, sulfonamides, quaternary ammonium compounds, triclosan, or metal ions based nanoparticles. With the broad application and abuse of such chemical biocides, there is a rising global threat of antimicrobial resistance to conventional treatments. Antimicrobial biomimetic surfaces based on cicada or dragonfly wings have been reported. These biomimetic surfaces comprising a plurality of nanospikes, such as disclosed in WO 2015/031956, show a great potential for antibacterial or other antimicrobial applications. Unlike when antibiotics or other chemical compounds are used to kill bacteria, the bactericidal effects of such nanomaterials come from the mechanical response of the nanostructures which kill microorganisms on contact. The antimicrobial effects come from the physical disruptions of cell walls induced by surface texturing and are independent on the surface chemical functionality; therefore such nanomaterials could reduce the risk of antimicrobial resistance or could be used in applications where e.g. bacteria have already developed resistance to traditional antibiotics.

There is however still room within the art for improving such antimicrobial surfaces in order to extend their range of potential applications and/or their biocidal properties.

SUMMARY

The present disclosure provides antimicrobial surfaces.

Some embodiments can obtain a large killing efficiency of microorganisms, such as bacteria.

Some embodiments allow a large variety of structures to be outfitted with the antimicrobial surface.

Some embodiments include an antimicrobial surface that is made up of a variety of materials.

Some embodiments include nanostructures of a surface that synergize with the effect of optional antimicrobial substances or compounds therein or therearound.

Some embodiments include an antimicrobial surface which is smooth to the touch. Surfaces composed of nanospikes having a pointy end tend to be rougher to the touch.

The above is accomplished by a method and device according to the present disclosure.

In a first aspect, the present disclosure relates to a structure comprising an antimicrobial surface on a substrate, the antimicrobial surface comprising a plurality of nanostructures, each nanostructure comprising:

a nanopillar on the substrate, the nanopillar having a height, and (ii) a head covering a distal end and at least part of the height of the nanopillar.

The nanopillars may participate in the antimicrobial effect when they are not entirely covered by the heads but their primary function is to serve as a template for the formation of the head and to fix the heads in place. Nanopillars can be formed at well-defined positions on a substrate by processes such as lithography. Once the nanopillars are formed at the desired places with the desired spacing, they can be used as template to form the heads thereon. The end result is a plurality of heads fixed at well-defined positions with respect to the substrate.

In a second aspect, the present disclosure relates to a use of the structure according to any embodiment of the first aspect for killing and/or inhibiting the growth of a microorganism.

In a third aspect, the present disclosure relates to a method for making a structure comprising an antimicrobial surface on a substrate, comprising:

a1. providing a substrate with a plurality of nanopillars thereon, each nanopillar having a height (H), and b1. forming a head at a distal end of each nanopillar, the head covering the distal end and at least part of the height of o the nanopillar on which it is formed.

In a fourth aspect, the present disclosure relates to the use of a structure for killing and/or inhibiting the growth of a microorganism, the structure comprising a surface on a substrate, the surface comprising gaps having a width (w), measured parallel to the substrate at at least one position along the height ($h_G$) of the gaps, of from 2 nm to 400 nm, such as from 2 to 40 nm, such as from 2 to 20 nm, such as from 2 to 10 nm and a depth (d) measured from the position to the substrate of at least 10 nm.

In a further aspect, the present disclosure relates to a structure comprising an antimicrobial surface on a substrate, the antimicrobial surface comprising a plurality of nanoparticles having a width (Wh) of from 20 to 400 nm, packed in such a way that gaps exists in the surface, between nanoparticles, having a width (w), measured parallel to the substrate at at least one position along the height ($h_G$) of the gaps, of from 2 nm to 400 nm, such as from 2 to 40 nm, such as from 2 to 20 nm, such as from 2 to 10 nm and a depth (d) measured from the position to the substrate of at least 10 nm, the structure further comprising a coating layer covering the nanoparticles, the coating layer being thinner than the width of the particles and, in some embodiments, thinner than half the width of the particles.

Particular aspects are set out in the accompanying independent and dependent claims. Features from the dependent claims may be combined with features of the independent claims and with features of other dependent claims as appropriate and not merely as explicitly set out in the claims.

Although there has been constant improvement, change and evolution of devices in this field, the present concepts are believed to represent substantial new and novel improvements, including departures from prior practices, resulting in the provision of more efficient, stable and reliable devices of this nature.

The above and other characteristics and features will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

BRIEF DESCRIPTION OF THE DRAWINGS

FIG. 6A illustrates a cross-sectional scanning electron image of a nanostructured surface according to a comparative example, but which could be used as nanopillars to form nanostructures, according to example embodiments.

FIG. 6B illustrates a cross-sectional scanning electron image of a nanostructured surface according to a comparative example, but which could be used as nanopillars to form nanostructures, according to example embodiments.

FIG. 7A illustrates a cross-sectional scanning electron image of a nanostructured surface according to a comparative example, but which could be used as nanopillars to form nanostructures, according to example embodiments.

FIG. 7B illustrates a cross-sectional scanning electron image of a nanostructured surface according to a comparative example, but which could be used as nanopillars to form nanostructures, according to example embodiments.

FIG. 16A illustrates a cross-sectional scanning electron image of a surface that includes a plurality of nanopillars as an intermediate to a structure, according to example embodiments.

FIG. 16B illustrates a cross-sectional scanning electron image of the structures of FIG. 16A after the performance of step b1 of a method, according to example embodiments.

FIG. 17 illustrates a bar graph of the *E. coli* killing efficiency of a structure according to example embodiments where the head covers the complete height of the nanopillar, compared to comparative examples and to other example embodiments where the head covers only part of the height of the nanopillar.

FIG. 18A illustrates a step of a method, and a top view, scanning electron image of a sample after the step of the method, for forming a structure where the head covers the complete height of the nanopillar, according to example embodiments.

FIG. 18B illustrates a step of a method, and a top view, scanning electron image of a sample after the step of the method, for forming a structure where the head covers the complete height of the nanopillar, according to example embodiments.

FIG. 18C illustrates a step of a method, and a top view, scanning electron image of a sample after the step of the method, for forming a structure where the head covers the complete height of the nanopillar, according to example embodiments.

FIG. 19 schematically illustrates two alternative methods for forming a structure, according to example embodiments.

Figure 1:
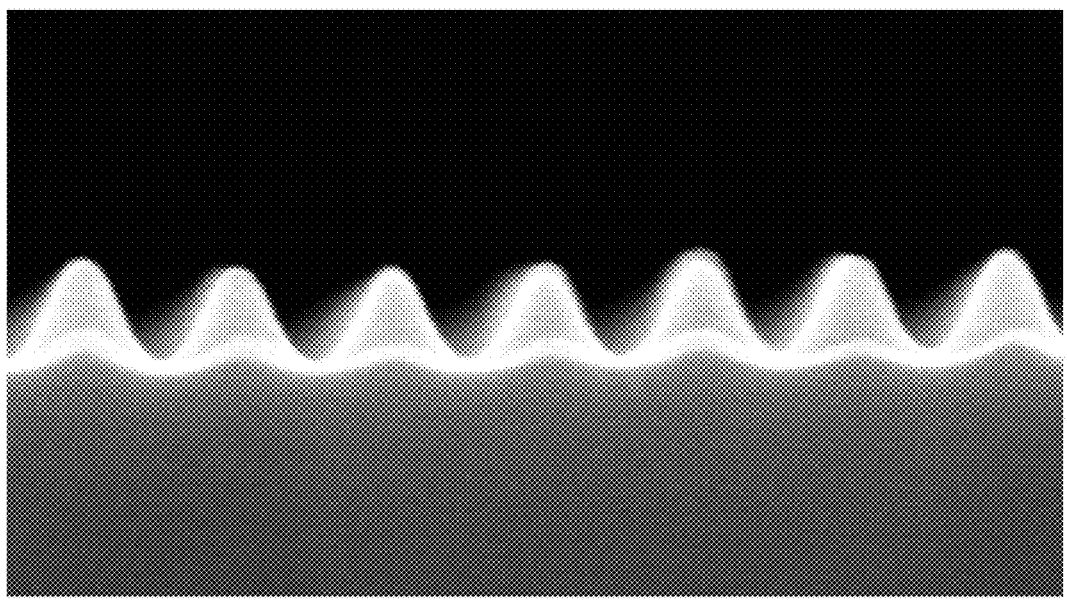
FIG. 1 illustrates a cross-sectional scanning electron image of different nanostructured surfaces according to comparative example, but which could be used as nanopillars to form nanostructures, according to example embodiments.

In the different figures, the same reference signs refer to the same or analogous elements.

DETAILED DESCRIPTION

The present disclosure will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice.

Furthermore, the terms first, second, third and the like in the description and/or in the claims, are used for distinguishing between similar elements and not necessarily for describing a sequence, either temporally, spatially, in ranking or in any other manner. It is to be understood that the terms so used are interchangeable under appropriate circumstances and that the embodiments described herein are capable of operation in other sequences than described or illustrated herein.

Moreover, the terms top, bottom, over, under and the like in the description and/or the claims are used for descriptive purposes and not necessarily for describing relative positions. It is to be understood that the terms so used are interchangeable under appropriate circumstances and that the embodiments described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a composition comprising elements A and B" should not be interpreted as being limited in scope to compositions consisting only of components A and B. It means that with respect to the present embodiment, the only relevant elements of the composition are A and B.

Reference throughout this specification to "one embodiment" or "an embodiment" means that a particular feature, structure or characteristic described in connection with the embodiment is included in at least one embodiment. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of example embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment.

Furthermore, while some embodiments described herein include some but not other features included in other embodiments, combinations of features of different embodiments are meant to be within the scope of the disclosure, and form different embodiments, as would be understood by those in the art. For example, in the following claims, any of the claimed embodiments can be used in any combination.

In the description provided herein, numerous specific details are set forth. However, it is understood that some embodiments may be practiced without these specific details. In other instances, well-known methods, structures and techniques have not been shown in detail in order not to obscure an understanding of this description.

As used herein, and unless provided otherwise, an antimicrobial surface is a surface which kills microorganisms or inhibits their growth. For example, the antimicrobial surfaces of the present disclosure kill microorganisms. The surface may for example be antibacterial, antiviral and/or antifungal, i.e. the surface may act against bacteria, viruses and/or fungi. In some embodiments, the antimicrobial surface may be at least an antibacterial surface. The antibacterial efficiency may be such that at least 95%, such as at least 99% of a 40 µl inoculum of E. coli at 37° C. having a concentration of $10^6$ CFU/ml is killed in 3H.

As used herein, and unless provided otherwise, the term "synthetic", when used to characterize an object, means that the object is an artifact (e.g. it is man-made or machine-made), as opposed to an object occurring in nature (such as on an insect wing). For instance, a synthetic surface is an artifact. A synthetic surface may also be referred to as a man-made or artificial surface.

As used herein, and unless provided otherwise, the distal end of a nanopillar or nanopillar portion is the end away from its point of attachment to the substrate.

As used herein, and unless provided otherwise, the width of a structure is its shortest dimension parallel to the surface of the substrate on which the structure stands; the length of a structure is its longest dimension parallel to the substrate on which the structure stands; frequently, in the present disclosure, when it is referred to nanopillars, both dimensions parallel to the substrate are equal and we do not refer to the length; the height of a structure is its longest dimension perpendicular to the surface of the substrate on which is stands.

As used herein, and unless provided otherwise, a maximum width of a structure, e.g. of a head, is the width of the structure at its widest point.

As used herein, and unless provided otherwise, an average width of a structure, e.g. of a nanopillar portion, is calculated by averaging the width along the height of the structure.

As used herein, and unless provided otherwise, a "head" is a nanoparticle covering the distal end of a nanopillar and at least part of its height. The term head will herein be used, for example, when a nanopillar is present on which the nanoparticle has been formed. When no nanopillar is present and the nanoparticle is directly on the surface, the term "nanoparticle" may be used.

As used herein, and unless provided otherwise, a "nanopillar portion" is that portion of the nanopillar which is not covered by the head.

In a first aspect, the present disclosure relates to a structure comprising an antimicrobial surface on a substrate, the antimicrobial surface comprising a plurality of nanostructures, each nanostructure comprising either:
  i. a nanopillar on the substrate, the nanopillar having a height, and
  ii. a head covering a distal end and at least part of the height of the nanopillar.
or
  i. a nanopillar portion on the substrate, the nanopillar portion having an average width, and
  ii. a head on a distal end of the nanopillar portion, the head having a (maximum) width;
wherein the (maximum) width of the head is larger than the average width of the nanopillar portion.

Typically, the structure is composed of a substrate and of nanostructures present on a surface thereof. In that case, the surface and the nanostructures thereon form the antimicrobial surface.

The structure comprising the antimicrobial surface of the present disclosure can be any structure. In particular, it can be an artifact. For instance, it may be but is not limited to, a bandage, an implant, a wall, a handle (e.g. a door handle), a container, etc.

Typically, the antimicrobial property of the surface may be biophysical in nature, i.e. it may be the physical interactions of the nanostructures with the microorganism which kills it or inhibits its growth. In some embodiments, the antimicrobial property of the surface may be both biophysical and biochemical in nature, a chemical interaction of the nanostructures with the microorganism may participate in the killing of the microorganisms or the inhibition of their growth. The nanostructure may for example comprise an antimicrobial substance, such as a metal (e.g. Ag, Au or Cu) or a metal oxide (e.g. hafnium oxide ($HfO_x$) or aluminium oxide ($AlO_x$)). The nanopillar portion and/or head may for instance each independently comprise an antimicrobial substance, or the nanopillar portion and/or head may be covered by a layer of the antimicrobial substance. The nanostructure may then act against the microorganism in a physical way by virtue of its shape, while the antimicrobial substance may act against the microorganism in a chemical way. These effects may typically be synergistic, i.e. the effect of the combination of biophysical and biochemical interactions may exceed the sum of its parts. The biophysical interactions provided by the structures according to the present disclosure are however sufficient to already show a significant antimicrobial activity. Therefore, in some embodiments, the nanostructure does not comprise a material which chemical nature renders it antimicrobial (e.g. antibacterial).

Without being bound by theory, our experiments suggest that the mechanism behind the surprising observed antimicrobial effect of the structures of the present disclosure is that the contact between the cell wall and/or membrane of a microorganism, such as a bacterium, and the surface comprising the nanostructures (particularly the gaps between the heads) may cause physical stress to the cell wall and/or membrane, e.g. as the microorganism moves or flows over the antimicrobial surface. This physical stress can in turn lead to rupturing the cell wall and/or membrane. Is some embodiments where heads are present on thinner nanopillar portions, a pocket is created between two nanostructures in which part of the microorganism may "fall into," in turn increasing the stress on the cell wall and/or membrane. In these embodiments, a high aspect ratio pillar or a pillar made of a flexible material may offer a degree of flexibility and movement to the head, which can again lead to additional stress and even to "pinching" of the microorganism in between two adjacent heads. However, we could demonstrate that the antimicrobial effect is equally excellent in embodiments where the nanopillar are entirely covered with the head, indicating that the presence of the thinner nanopillar portions is are not absolutely necessary and that it is the heads and the gaps between them that play the most important role.

The surface is typically a synthetic surface. The nanostructures are typically synthetic nanostructures.

The chemical nature of the substrate is typically not determinant for the antimicrobial effect and does not play a preponderant role in the antimicrobial properties of the structure. The same holds true for the chemical nature of the nanostructures.

In embodiments, the plurality of nanostructures may be arranged randomly on the substrate. In other embodiments, the plurality of nanostructures may be an array of nanostructures, i.e. an orderly arrangement of nanostructures. For instance, each nanostructure not belonging to the edges of the array may have a same number of adjacent nanostructures. In an embodiment, each nanostructure simultaneously may belong to a line of equidistant nanostructures and to a column of equidistant nanostructures. As a particular example, the nanostructures may be arranged to form a rectangular (e.g. a square) grid wherein each nanostructure occupies a corner of a square in the grid. Of course, what is said in the present paragraph for the array of nanostructures, also holds true for the nanopillars (and hence the nanopillar portions) comprised in the nanostructures.

In embodiments, the plurality of nanostructures may comprise at least two nanostructures. In embodiments, the plurality of nanostructures may comprise at least 4 nanostructures. In other embodiments, the plurality of nanostructures may comprise at least 9 nanostructures. In yet other embodiments, the plurality of nanostructures may comprise at least 25 nanostructures. In yet other embodiments, the plurality of nanostructures may comprise at least 64 nanostructures. In yet other embodiments, the plurality of nanostructures may comprise at least 1000 nanostructures or at least 10000 nanostructures.

In embodiments, the number of nanostructures typically does not have an upper limit as it scales with the surface area of the surface of the structure to be made antimicrobial. For instance, up to $1 \times 10^{12}$ nanostructures, or even more, can readily be achieved.

In embodiments, the density of nanostructures on the substrate may be from $1 \times 10^8$ to $1 \times 10^{12}$ nanostructures per $cm^2$. In other embodiments, the density of nanostructures on the substrate may be from $1 \times 10^9$ to $1 \times 10^{11}$ nanostructures per $cm^2$.

In embodiments, the distance between corresponding points of two adjacent nanostructures (e.g. between corresponding points of two nanopillar portions or between corresponding points of two adjacent heads) within the plurality of nanostructures may be in average from 20 to 500 nm. In another embodiment, this distance may be in average from 25 to 200 nm. In yet other embodiments, this distance may be in average from 30 to 100 nm, such as 90 nm. In yet other embodiments, this distance may be in average from 30 to 50 nm. A smaller distance between corresponding points of two adjacent nanostructures translates in a higher density of nanostructures and hence into a higher density of gaps in the antimicrobial surface. Since these gaps are believed to play an important role in the antimicrobial properties, a higher density thereof is believed to be beneficial.

In embodiments, each nanostructure may belong to a line of equidistant nanostructures separated by a distance between corresponding points of two successive nanostructures along the line of from 20 to 500 nm. In another embodiment, the distance may be from 25 to 200 nm. In yet other embodiments, the distance may be from 30 to 100 nm, such as 90 nm. In yet other embodiments, the distance may be from 30 to 50 nm. Simultaneously to belonging to a line of equidistant nanostructures separated as just mentioned, each nanostructure may belong to a column of equidistant nanostructures separated by a distance between corresponding points of two successive nanostructures along the line of from 20 to 500 nm, 25 to 200 nm, 30 to 100 nm (such as 90 nm), or 30 to 50 nm. In some embodiments, this separation distance in the lines and the columns may be the same.

Each nanostructure comprises (and typically consist of) a nanopillar and a head covering an end of the nanopillar portion and at least part of the height of the nanopillar.

In embodiments, where the head only covers part of the height of the nanopillar, thereby defining an uncovered nanopillar portion, each nanostructure comprises a nanopillar portion and a head at an end of the nanopillar portion, the head having a width larger than the average width of the nanopillar portion.

Figure 11:
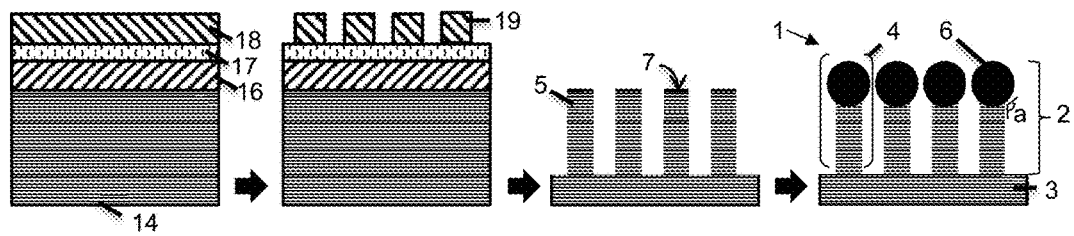
FIG. 11 schematically illustrates a method for forming a structure, according to example embodiments.

When a nanopillar portion is present, the head of the nanostructure can typically be distinguished therefrom because of its position at the distal end of the nanostructure and because of its width, larger than the average width of the nanopillar portion. In some embodiments, the head can further be identified by its round shape. In some embodiments, the head can further be identified by it being formed of another material than the nanopillar portion. Along the height of the nanostructure, the nanopillar portion ends where the head starts. Typically, at the point of contact between the nanopillar portion and the head, the lower part of the head is at an angle a of from 70 to 150°, such as from 80 to 140°, such as from 90 to 140° with the upper part of the nanopillar portion. This is illustrated in FIG. 11.

Each nanopillar and each nanopillar portion has a proximal extremity on the substrate and a distal extremity away from the substrate. Typically, averaged over the plurality of nanopillar portions, the angle between the nanopillar portions and the substrate on which they stand is from 30 to 90°, such as from 45° to 90°, such as from 60° to 90°, such as from 80° to 90°. For instance, the nanopillar portions may stand perpendicularly to the surface of the substrate on which they stand. In embodiments, where the nanopillar portions are flexible, this angle is determined when the nanopillars are at rest, i.e. in absence of external forces other than gravitation, and when the substrate assumes a horizontal position.

In embodiments, the nanopillar portions may exhibit a level of flexibility so as to enable the heads of adjacent nanostructures to touch each other, without fracturing the nanopillars. Separation of adjacent nanostructures can be controlled by controlling atmospheric humidity, surface wetting and surface treatment with, solvents, for example. In embodiments, the nanopillar portions may be characterised by a Young's modulus of elasticity of from about 10 GPa to about 300 GPa, such as form about 50 GPa to about 200 GPa or from about 100 GPa to about 150 GPa.

According to some embodiments, the present disclosure relates to a structure as described in any embodiment of the first aspect, wherein a majority of the nanostructures have their head in contact with the head of at least one other nanostructure (of the plurality). When the heads are in contact, gaps exist between adjacent nanostructures that are smallest in size. In our experiments, such small gaps have a positive effect on the antimicrobial effect.

When the surface comprises a plurality of heads, having a width (Wh) of from 20 to 400 nm, packed in such a way that gaps exists between adjacent heads, which gaps having a width (w), measured parallel to the substrate at at least one position along the height ($h_G$) of the gaps, of from 2 nm to 400 nm, such as 2 to 40 nm, such as from 2 to 20 nm, such as from 2 to 10 nm and a depth (d) measured from the position to the substrate of at least 10 nm, the best antimicrobial effects have been observed.

In embodiments, the depth of the gaps measured toward the substrate may be at least 20 nm.

In embodiments, the area covered by the gaps at the at least one position along the height ($h_G$), may represent at least 1% of the area of the structure at that height ($h_G$). For instance, it may represent from 1 to 50% and more typically from 1 to 15%, from 1 to 10% or from 1 to 8% of the area of the structure at that height (parallel to the substrate).

The packing density of the heads, i.e. the proportion of the surface covered by the heads, may be at least 0.85 (the gaps cover at most 15% of the surface), such as at least 0.90 (the gaps cover at most 10% of the surface), such as at least 0.92 (the gaps cover at most 8% of the surface). The close packing of spherical heads permits a maximum packing density of 0.9069 when the packing is hexagonal. However, a larger maximum packing density can be achieved when the heads adopt a more cubic shape (see surface no 5 in the examples, FIG. 18C and FIG. 21). A high packing density typically translates in smaller gaps in the surface, between the heads.

The packing density is however smaller than 1.00. A packing density of 1.00 is for instance theoretically achievable with cubic heads. Such a packing density however does not present gaps susceptible to kill the microbes. The packing density may be smaller than 0.99.

The extent of the gaps and the packing density are measured by taking a picture of the surface from the top, and by measuring the extent of the gaps and the packing density visible on that picture. This is shown in schematic form in FIGS. 20 and 21 where gaps between nanostructures/heads are measured and where the area taken by the white portions of the images (particles (e.g. heads)) divided by the area taken by both the white and the black areas of the images (particles (e.g. heads)+gaps) is measured. The gaps measured on the picture may correspond in the structure to a gap situated at least 10 nm or even at least 20 nm above the substrate. This permits parts of the microbe to fall into the gap in a way that is detrimental for its survival. If the heads are spherical, a diameter (i.e. a width) of 20 nm for the head assures that the distance between the gap as measured and the substrate is 10 nm (in absence of nanopillar portion). In the case of cubic nanoparticles having a width of 20 nm, the distance between the gap as measured and the substrate is 20 nm (in absence of nanopillar portion). This distance from the substrate can be increased by the presence of a nanopillar portion.

In embodiments, the at least one position may be within 50 nm of the top of the surface.

Each nanopillar or nanopillar portion is typically an elongated object. In view of the definitions of width, length and height used herein, this means that each nanopillar or nanopillar portion is typically higher (dimension perpendicular to the substrate) than it is wide (shortest dimension parallel to the substrate) of long (longest dimension parallel to the substrate). In embodiments, it has a cross-section taken perpendicularly to the length of the nanopillar portion which is circular or has a cross-section taken perpendicularly to the length of the nanopillar portion which is rectangular (e.g. square). In other words, in some embodiments, each nanopillar portion may for example typically be elongated and have a cylindrical or a (rectangular) cuboidal shape.

In embodiments, the average width (diameter in the case of a cylindrical nanopillar portion) of each nanopillar portion may be from 10 to 300 nm, such as from 20 to 100 nm, such as from 30 to 70 nm, such as 30 to 50 nm, such as 35 to 45 nm. This average width is calculated by averaging the width along the height of the nanopillar portion. In embodiments, a maximum width of the nanopillar portion may be up to 10 times larger than a minimum width of the same nanopillar portion, such as up to 5 times larger, such as up to 3 times larger, such as up to 2 times larger.

In embodiments, the nanopillar portions may have a constant width along their length.

In other embodiments, their width may vary along their length. For instance, in some embodiments, the nanopillar portions may have a larger width at their proximal extremity than at mid-height. For instance, the nanopillar portions may be shaped like pyramids or like cones with the base of the pyramids or cones being on the substrate. The nanopillar portions may also be shaped like truncated pyramids or truncated cones where the truncation is operated parallel to the base, thereby defining a smaller base in addition to the original base which becomes the largest base. In that last case, the largest base of the pyramids may be on the substrate. Embodiments where nanopillar portions have a larger width at their proximal extremity than at mid-height are typical of a manufacture by lithography. This increases the mechanical stability of each nanopillar portion but it is not believed to play a role in the antimicrobial effect.

In embodiments, the height of each nanopillar portion may be from 0 to 800 nm. 0 nm corresponds to the absence of a nanopillar portion. When a nanopillar portion is present, it may for instance have a height of 40 to 800 nm, such as from 50 to 700 nm (e.g., 700 nm), such as from 100 to 650, such as from 200 to 600 (e.g., 330 nm, 580 nm, or 600 nm). For example, the heights of the nanopillar portions forming the plurality of nanopillar portions may be within 30% of each other, such as within 15%, such as within 5% of each other. Preferably, they all have substantially the same height. This helps in achieving a smooth and flat surface.

In embodiments, the height (H) of each nanopillar may be from 10 to 840 nm, such as from 40 to 840 nm, such as from 50 to 740 nm (e.g., 700 nm), such as from 100 to 650, such as from 200 to 600 (e.g., 330 nm, 580 nm, or 600 nm). For example, the heights of the nanopillar portions forming the plurality of nanopillar portions may be within 30% of each other, such as within 15%, such as within 5% of each other. For example, they all have substantially the same height. This helps in achieving a smooth and flat surface.

Similarly, for example, the heights of the nanopillars forming the plurality of nanopillars may be within 30% of each other, such as within 15%, such as within 5% of each other. In some embodiments, the nanopillars could all have substantially the same height (e.g., within 1% of each other or less). This helps in achieving a smooth and flat surface.

In embodiments, the head may have at least an upper portion having the shape of a convex curved surface. In embodiments, the head may be a round head. The head may for example be ellipsoidal (e.g. spheroidal or spherical). The head may also be rectangular.

Typically, the ratio width/length and the ratio width/height of the head are both from 0.7 to 1.3, such as from 0.8 to 1.2, such as from 0.9 to 1.1.

In embodiments, the (maximum) width of the head may be from 25 to 510 nm, such as from 55 to 210, such as from 70 to 110 nm, such as 100 nm. In embodiments, the (maximum) width of the head may be at least 1.5 times larger than the average width of the nanopillar portion, such as at least 2 times larger, such as at least 3 times larger. In embodiments, the space between two adjacent heads may be in average from 50 to 0 nm, such as from 20 to 0 nm, such as from 10 to 0 nm. Two adjacent heads may for example be touching each other.

In embodiments, a height of the nanostructure (i.e. the combination of nanopillar portion, if present, and head) may be from 10 to 1500 nm, such as from 25 to 1500 nm, such as from 55 to 1500.

In embodiments where a nanopillar portion is present, a height of the nanostructure (i.e. the combination of nanopillar portion and head) may for instance be from 60 to 1500 nm, such as from 100 to 1000 nm, or from 270 to 710 nm.

In embodiments where a nanopillar portion is not present, a height of the nanostructure (i.e. head alone) may for instance be from 10 to 200 nm, such as from 25 to 150 nm, or from 55 to 100 nm.

In embodiments, the height of the head may represent from 5 to 100% of the height of the nanostructure. In some embodiment, when a nanopillar portion is present, the height of the head may for instance represent 5 to 90%, 5 to 75%, 5 to 50%, 5 to 25%, or from 10 to 18% of the height of the nanostructure.

In embodiments, the nanostructure may comprise an inorganic material, such as Si (e.g. black Si). The nanopillar (and nanopillar portion) and/or head may for example each independently comprise an inorganic material. In embodiments, the nanostructure may consist of one or more inorganic materials. In embodiments, the nanostructure may consist of a single inorganic material. As an example, the nanostructure may consist in a $SiO_x$ (e.g. $SiO_2$) head and a Si nanopillar (and nanopillar portion).

In embodiments, the nanostructure may comprise an organic material, such as a polymer (e.g. polydimethylsiloxane, poly(methyl methacrylate) or polystyrene). The nanopillar portion and/or head may for example each independently comprise an organic material. In embodiments, the nanostructure may consist of one or more organic materials. In embodiments, the nanostructure may consist of a single organic material. In other embodiments, the nanostructure may consist of an organic nanopillar portion and an inorganic head. For instance, the nanopillar portion may be made of a polymer as defined above and the head may be made of $SiO_2$.

In embodiments, the nanostructure may comprise an antimicrobial substance.

In embodiments, the nanopillar portion and/or head may be hydrophilic. A nanopillar portion and/or head may for example be made hydrophilic by a treatment (e.g. a cleaning step) with ozone or an oxygen plasma. This works for instance for nanopillar portions and/or heads made of Si, $SiO_x$ or polystyrene. In other embodiments, the nanopillar portion and/or head may be hydrophobic. A nanopillar portion and/or head comprising Si or $SiO_x$ may be made hydrophobic by surface functionalization with silanes. A nanopillar portion and/or head comprising polystyrene (PS), e.g. originating from a block copolymer comprising a PS block, is hydrophobic but may be made hydrophilic by a treatment (e.g. a cleaning step) with ozone or an oxygen plasma.

According to some embodiments, the present disclosure relates to a structure as described in any embodiment of the first aspect, wherein a majority of the nanostructures have their head in contact with the head of at least one other nanostructure, such a structure being obtainable by contacting a structure as described in any embodiment of the first aspect with a liquid, followed by drying the structure.

According to some embodiments of the first aspect, the present disclosure relates to a structure comprising an antimicrobial surface on a substrate, the surface comprising a plurality of nanostructures, each nanostructure being obtainable by depositing by physical vapor deposition or chemical vapor deposition a material on top of nanopillars until a head having a width larger than the average width of the nanopillars is formed at a distal end of the nanopillars. This head covers the distal end and may cover all or part of the height of the nanopillar.

According to some embodiments of the first aspect, the present disclosure relates to a structure comprising an antimicrobial surface on a substrate, the surface comprising a plurality of nanostructures, each nanostructure being obtainable by depositing by sputtering a material on top of nanopillars until a head having a width larger than the average width of the nanopillars is formed at a distal end of the nanopillars. This head covers the distal end and may cover all or part of the height of the nanopillar.

According to some embodiments of the first aspect, the present disclosure relates to a structure comprising an antimicrobial surface on a substrate, the surface comprising a plurality of nanostructures, each nanostructure being obtainable by depositing by sputtering $SiO_2$ on top of nanopillars until a head having a width larger than the average width of the nanopillars is formed at a distal end of the nanopillars. This head covers the distal end and may cover all or part of the height of the nanopillar.

According to some embodiments of the first aspect, the present disclosure relates to a structure comprising an antimicrobial surface on a substrate, the surface comprising a plurality of nanostructures, each nanostructure being obtainable by depositing by sputtering $SiO_2$ on top of Si nanopillars until a head having a width larger than the average width of the nanopillars is formed at a distal end of the nanopillars. This head covers the distal end and may cover all or part of the height of the nanopillar.

In a second aspect, the present disclosure relates to a use of the structure according to any embodiment of the first aspect for killing and/or inhibiting the growth of a microorganism.

In embodiments, the microorganism may be a bacteria, a virus, or a fungus. In some embodiments, the microorganism may have a cellular membrane (e.g., if the microorganism is a bacteria or a fungus). In some embodiments, the microorganism may be a bacteria. For instance, the microorganism may be *Escherichia coli*.

In embodiments, the use of the structure of the first aspect may be in combination with an antimicrobial substance, such as an antibiotic. The antimicrobial substance can for instance be applied on the antimicrobial surface of the structure. The nanostructures may increase the effect of the antimicrobial substance, e.g. by increasing the uptake of the antimicrobial substance by the microorganism. This interaction may be synergistic.

In a third aspect, the present disclosure relates to methods for making a structure comprising an antimicrobial surface on a substrate.

Figure 12:
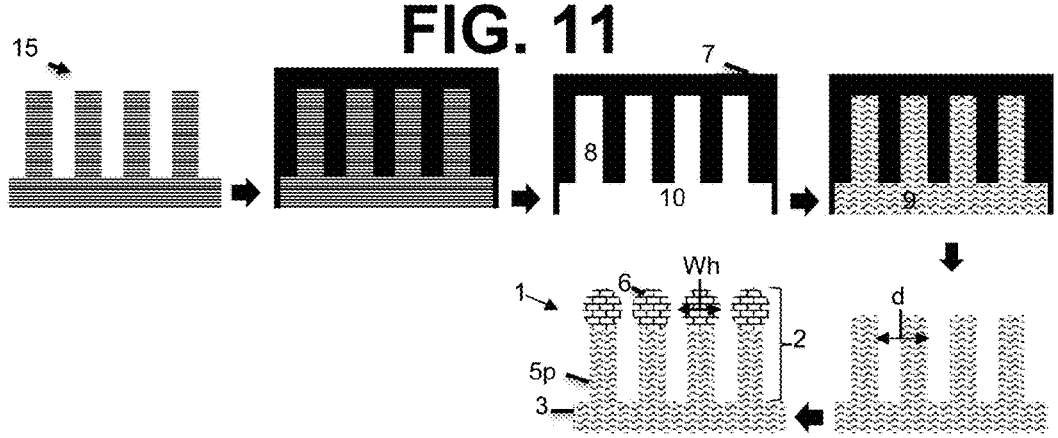
FIG. 12 schematically illustrates a method for forming a structure, according to example embodiments.
Figure 14:
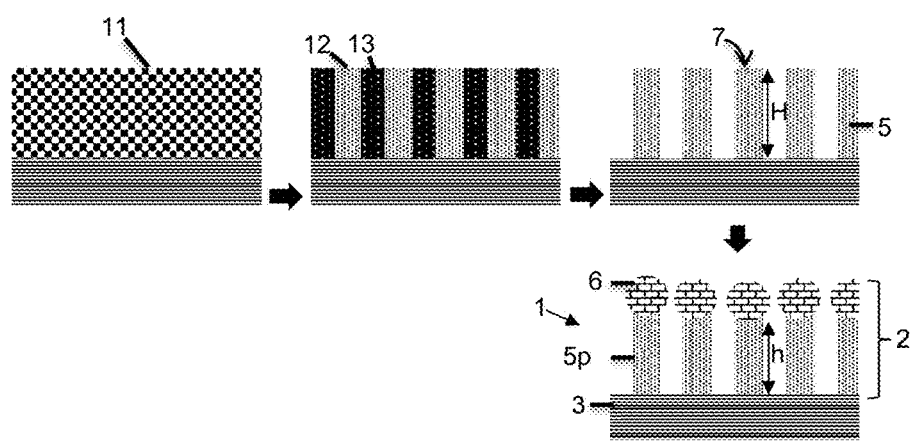
FIG. 14 schematically illustrates a method for forming a structure, according to example embodiments.

A first method, for instance illustrated in FIGS. 11, 12, and 14, may comprise:
  a1. providing a substrate (3) with a plurality of nanopillars (5) thereon, each nanopillar (5) having a height (H), and
  b1. forming a head (6) at a distal end of each nanopillar (5), the head (6) covering the distal end (7) and at least part of the height (H) of the nanopillar (5) on which it is formed.

In embodiments where the head (6) is only covering part of the height (H) of the nanopillar (5), the method may comprise:
  a1. providing a substrate (3) with a plurality of nanopillars (5) thereon, and
  b1. forming a head (6) on a distal end (7) of each nanopillar (5), the head (6) having a width (Wh), thereby defining a nanopillar portion (5*p*) as being the portion of each nanopillar (5) which is not covered by the head (6); wherein the width (Wh) of the head (6) is larger than the average width of the nanopillar portion (5*p*).

In this first method, the nanopillars (5) provided in step a1 have a height H which is in typical embodiments larger than the height h of the nanopillar portions (5*p*) obtained after formation of the head portion (6). Indeed, during its formation at the distal end (7) of the nanopillar (5), the head portion (6) typically covers part of the sidewall of the nanopillar at that distal end (7), thereby defining a nanopillar portion (5*p*) having a lower height than the original nanopillar (5). It is however noteworthy that the material that will form the head deposits itself typically more easily on the top of the nanopillars than on its sidewalls, thereby favouring the formation of the head instead of favouring the formation of a conformal coating of the nanopillars. This is illustrated in FIG. 14. Except for their respective height, which are typically different, and for their average width, which are averaged over their height, and which can therefore also be slightly different, all other characteristics of the nanopillars are typically the same as the characteristics of the corresponding nanopillar portions. Since the difference in height can in some embodiments be negligible (e.g. when the height of the nanopillar portion is 90% or more of the height of the nanopillar), what is said about nanopillar portions in the present disclosure, including what is said of their height or average width, can also apply to nanopillars, and vice versa.

It is noteworthy that the structure obtained before step b1, already show interesting antibacterial properties. These antimicrobial properties are improved after step b1.

In embodiments, for instance illustrated in FIG. 11, step a may comprise patterning and etching of a substrate (14) (e.g. Si) such as to obtain the nanopillars (5).

In other embodiments, for instance illustrated in FIG. 12, step a1 may comprise:
  a2. providing a mold (7) for a plurality of nanopillars (5), the mold comprising a substrate-shaped cavity (10) and a plurality of nanopillar-shaped cavities (8) opening therein, the nanopillar-shaped cavities (8) having an average width,
  b2. filling the mold (7) with a precursor material (9),
  c2. Optionally hardening the precursor material (9), and
  d2. removing the mold (7) from the precursor material (9) or the hardened precursor material.

Here the term "substrate-shaped cavity" means that the shape of the cavity is the negative of the shape of a substrate. For instance, it may be the negative of the shape of a hexahedron.

Here the term "nanopillar-shaped cavities" means that the shape of the cavity is the negative of the shape of a nanopillar in any embodiment herein.

Fabrication of flexible antimicrobial surfaces in soft materials could have more commercial potentials than rigid antimicrobial surfaces. For instance, flexible surfaces would allow the formation of antiseptic band aids or the formation of a coating on body-implanted materials, food packaging, surgical tools, filters, or on surfaces in public areas.

In embodiments, the mold may comprise an inorganic material. An inorganic material is typically a rigid material and the cavities may be formed directly therein, e.g. by etching. In other embodiments, the mold may comprise an elastomeric material. An elastomeric mold is elastic and it may therefore be easier to remove the hardened material from the mold. However, cavities can typically not be directly formed in the elastomeric material. To form an elastomeric mold, as for example illustrated in the first two steps of FIG. 12, a first (rigid) negative (15) of the mold (7) may first be made comprising a plurality of nanopillars and the elastomeric mold (7) may then be formed therearound.

In embodiments, the precursor material may be a polymer (e.g. polydimethylsiloxane, poly(methyl methacrylate) or an epoxy resin) or a precursor thereto. In embodiments, hardening the precursor material may comprise curing the precursor material. In embodiments, the substrate may be formed together with the plurality of nanopillars. The mold may for example further comprise a substrate cavity, the plurality of cavities opening up therein, or the mold may be overfilled; thereby forming the plurality of nanopillars connected to the substrate.

In embodiments, the material of the mold, the precursor material and the hardening of the precursor material may independently be as correspondingly described for embodiments of the first method.

In embodiments, the substrate may be formed together with the plurality of nanostructures. The mold may for example further comprise a substrate cavity, the nanopillar-shaped cavities opening up therein, or the mold may be overfilled; thereby forming the plurality of nanostructures connected to the substrate.

In other embodiments, for instance illustrated in FIG. 14, step a may comprise phase separating a layer (11) of a block copolymer into a cylindrical phase (12) and a non-cylindrical phase (13), followed by removing the non-cylindrical phase (13). For instance, the block copolymer may be a poly(methyl methacrylate)-b-polystyrene (PMMA-b-PS) block copolymer and the cylindrical phase (12) may be a PS phase. In these embodiments, step a1 may further comprise infiltrating the cylindrical phase (12) with a metal or ceramic material (e.g. through a sequential infiltration synthesis). This step is not represented in FIG. 14. It is noteworthy that the structure obtained before step b1, already show interesting antibacterial properties. These antimicrobial properties are improved after step b1.

In embodiments, step b1 may comprise depositing (e.g. by sputtering or chemical vapor deposition) a material (e.g. a metal such as Cu, Ag or Au or an oxide such as $SiO_x$, $HfO_x$, $TiN_x$, $AlO_x$, wherein x is at least 0.1) on top of the nanopillars. Depositing a material by sputtering or chemical vapor deposition on top of nanopillars tend to automatically form a head at the distal ends of the nanopillars. To the best of our knowledge, this does not depend on the sputtering or deposition conditions.

Figure 13:
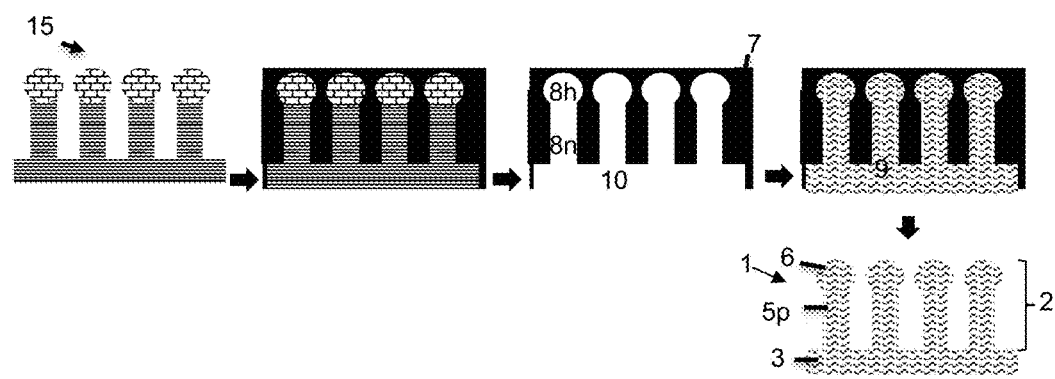
FIG. 13 schematically illustrates a method for forming a structure, according to example embodiments.

A second method, for instance illustrate in FIG. 13, may comprise:

a2. providing a mold (7) for a plurality of nanostructures (4), the mold being made of an elastomeric material and comprising a substrate-shaped cavity (10) and a plurality of nanostructure-shaped cavities (8) opening therein, each nanostructure-shaped cavity (8) comprising a nanopillar-shaped portion (8n) and a head portion (8p) on a distal end of the nanopillar-shaped portion (8n), the head portion (8h) having a width and the nanopillar-shaped portion (8n) having an average width, wherein the width of the head portion (8h) is larger than the average width of the nanopillar-shaped portion (8n), b2. filling the mold (7) with a precursor material (9), c2. Optionally hardening the precursor material (9), and d2. removing the mold (7) from the precursor material (9) or the hardened precursor material.

An elastomeric mold is elastic and may therefore be easier to remove the hardened material from the mold. However, cavities can typically not be directly formed in the elastomeric material. To form an elastomeric mold, as for example illustrated in the first two steps of FIG. 13, a first (rigid) negative (15) of the mold (7) may first be made comprising a plurality of the nanostructures and the elastomeric mold (7) may then be formed therearound.

In a fourth aspect, the present disclosure relates to the use of a structure for killing and/or inhibiting the growth of a microorganism, the structure comprising a surface on a substrate, the surface comprising gaps having a width (w), measured parallel to the substrate at at least one position along the height ($h_G$) of the gaps, of from 2 nm to 400 nm, such as from 2 to 40 nm, such as from 2 to 20 nm, such as from 2 to 10 nm and a depth (d) measured from the position to the substrate of at least 10 nm.

The gaps are for contacting the microorganism. Upon contact, the microorganism may die or see its growth inhibited but most typically dies.

In some embodiments, the at least one position along the height of the gaps is within 50 nm of the top of the surface. This may facilitate the contact of the effective part of the gap with the microorganism.

The gap does not need to fulfil the width requirement across its whole height. What matters is that the gap is narrow at least at one position where it contacts the microorganism. If the gap widens as it extends toward the substrate, this does not change the antimicrobial potency of the gap. If the gap widens as it extends toward the top of the surface, this does not change the antimicrobial potency of the gap provided this position of the gap is accessible to the microorganism, which will typically be the case if the at least one position is within 50 nm of the top of the surface.

Figure 22:
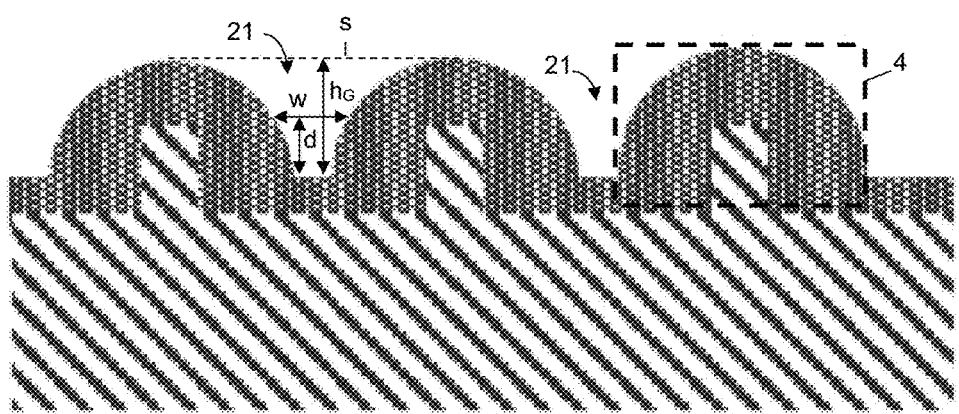
FIG. 22 is an enlarged portion of FIG. 18B, according to example embodiments.

FIG. 22 enlarges a portion of FIG. 18B and illustrates how one can determine whether a gap (21) fulfils its width and depth (d) requirements. The nanopillar in FIG. 22 has a width of about 35 nm and for the purpose of the present demonstration only, the figure is considered drawn to scale. As depicted on FIG. 22, there is a gap between two nanostructures (4). If the requirement is that the surface comprises gaps having a width (w), measured parallel to the substrate at at least one position along the height ($h_G$) of the gaps, of from 2 nm to 40 nm and a depth (d) measured from the position to the substrate of at least 10 nm, whether the gaps fulfil this requirement can be determined as follows. As indicated on the left side, the gap fulfils its width (w) and depth (d) requirements because a gap width (w) of 40 nm can be defined at the depicted position, and the depth (d) measured from the position to the substrate of at least 10 nm (here about 40 nm). We can also note that the at least one position along the height of the gap is within 50 nm of the top of the surface (s).

Figure 23:
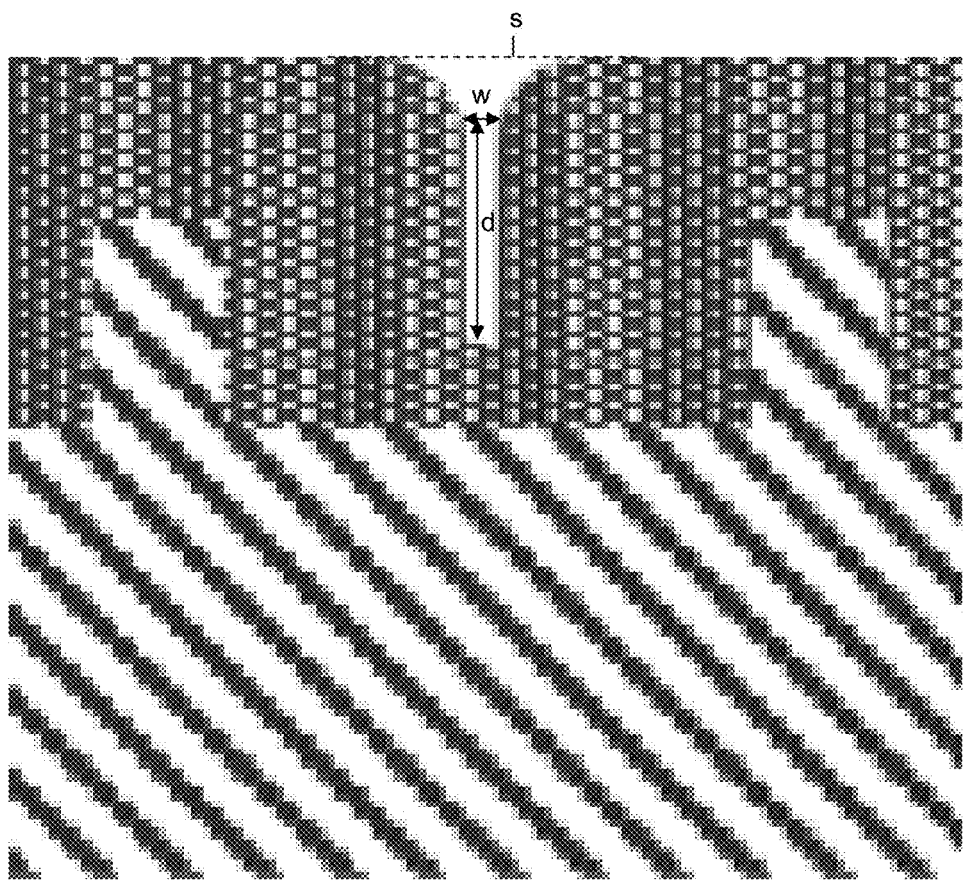
FIG. 23 is an enlarged portion of FIG. 18C, according to example embodiments.

FIG. 23 enlarges another portion of FIG. 18C and also illustrates how one can determine whether a gap (21) fulfils its width (w) and depth (d) requirements. The nanopillar in FIG. 23 has a width of about 35 nm and for the purpose of the present demonstration only, the figure is considered drawn to scale. As depicted on FIG. 23, there is a gap between two nanostructures. If the requirement is that the surface comprises gaps having a width (w), measured parallel to the substrate at at least one position along the height ($h_G$) of the gaps, of from of from 2 nm to 10 nm and a depth measured from the position to the substrate of at least 10 nm, whether the gaps fulfil this requirement can be determined as follows. As indicated on the figure, the gap fulfils its width (w) and depth (d) requirements because a gap width (w) of 9 nm can be defined at the depicted position, and the depth (d) measured from the position to the substrate is of at least 10 nm (here about 55 nm). We can also note that the at least one position along the height of the gap is within 50 nm of the top of the surface (s).

In embodiments, the surface may comprise a plurality of nanostructures (4) having a width (Wh) of from 20 to 400 nm, packed in such a way that the gaps exist between adjacent nanostructures (4).

In embodiments, the depth of the gaps measured toward the substrate may be at least 20 nm.

In embodiments, the gaps cover from 1 to 15% of the surface.

An alternative expression of the fourth aspect is therefore the use of a structure (1) for killing and/or inhibiting the growth of a microorganism, the structure comprising a surface (2) on a substrate (3), the surface comprising a plurality of nanostructures (4) having a width (Wh) of from 20 to 400 nm, packed in such a way that gaps exists in the surface, between nanostructures (4), wherein the gaps have a width (w), measured parallel to the substrate at at least one position along the height ($h_G$) of the gaps, of from 2 nm to 400 nm, such as from 2 to 40 nm, such as from 2 to 20 nm, such as from 2 to 10 nm and a depth (d) measured from the position to the substrate of at least 10 nm.

When the surface comprises nanostructures, the packing density of the nanostructures, i.e. the proportion of the surface covered by the nanostructures (e.g. nanoparticles), may be at least 0.85 (the gaps cover at most 15% of the surface), such as at least 0.90 (the gaps cover at most 10% of the surface), such as at least 0.92 (the gaps cover at most 8% of the surface). The close packing of spherical particles permits a maximum packing density of 0.9069 when the packing is hexagonal. However, a larger maximum packing density can be achieved when the particles adopt a more cubic shape (see surface no 5 in the examples, FIG. 18C and FIG. 21). A high packing density typically translates in smaller gaps in the surface, between the nanostructures.

Another alternative expression of the fourth aspect is therefore the use of a structure (1) for killing and/or inhibiting the growth of a microorganism, the structure comprising a surface (2) on a substrate (3), the surface comprising a plurality of nanostructures (4) having a width (Wh) of from 20 to 400 nm and having a packing density of at least 0.85, such as at least 0.90, such as at least 0.92. The packing density is however smaller than 1.00. A packing density of 1.00 is for instance theoretically achievable with cubic nanoparticles. Such a packing density however does not present gaps susceptible to kill the microbes. The packing density may be smaller than 0.99.

In embodiments, the area covered by the gaps at the at least one position along the height ($h_G$), may represent at least 1% of the area of the structure at that height ($h_G$). For instance, it may represent from 1 to 50% and more typically from 1 to 15%, from 1 to 10% or from 1 to 8% of the area of the structure at that height (parallel to the substrate).

In practice, the area covered by the gaps, the extent of the gaps, and the packing density are measured by taking a picture of the surface from the top, and by measuring the extent of the gaps and the packing density visible on that picture. This is shown in schematic form in FIGS. 20 and 21 where gaps between nanostructures are measured and where the area taken by the white portions of the images (particles) divided by the area taken by both the white and the black areas of the images (particles+gaps) is measured. The gaps measured on the picture may correspond in the structure to a gap situated at least 10 nm or even at least 20 nm above the substrate. This permits parts of the microbe to fall into the gap in a way that is detrimental for its survival. If the nanostructures are spherical nanoparticles, a diameter (i.e. a width) of 20 nm for the nanoparticles assures that the distance between the gap as measured and the substrate is 10 nm. In the case of cubic nanoparticles having a width of 20 nm, the distance between the gap as measured and the substrate is 20 nm.

The structure, the microorganism, the surface and the substrate may be as defined in any embodiment of the first aspect. In particular, the structure and the surface are artifacts, i.e. they are synthetic/man made. The nanostructures may comprise a nanopillar and a head as in the first aspect, or not. In this last case, the nanostructures may consist in nanoparticles. These nanoparticles may have any characteristic defined for the head in the first aspect. The shape of the nanostructure is not very critical as long as the gaps are present. For instance, the nanoparticles may be hemispherical, spherical, cubic, cylindrical or rectangular nanoparticles amongst others.

The surface comprising a plurality of nanoparticles can be formed on the substrate by first purchasing or synthesizing nanoparticles, then depositing them on the substrate, followed by fixing the particles on the substrate. The material of the nanoparticles is not critical. For instance, $SiO_x$ (e.g. $SiO_2$), $Si_3N_4$, polystyrene, or metal oxide particles can be used, amongst others. The particles can be monodisperse or polydisperse.

Depositing the particles on the surface can be performed by a large variety of methods. An example is detailed in example 8 (convective assembly) but methods based on capillarity, electrostatics, the use of surfactants, or the use of molecular interactions (e.g. DNA interactions) can be used. An example involving self-assembling a nanoparticle monolayer at a liquid-air interface, followed by draping it over a solid substrate is disclosed in K. E. Mueggenburg et al. (Nature materials, vol. 6, September 2007, p. 656-660).

Fixing the particles on the substrate can be performed in various ways. One way is to heat up the substrate with the particles thereon to achieve thermal bonding. Another way is to coat the particles with a coating layer, thinner than the width of the particles or even thinner than half the width of the particles. A combination of both method can also be used.

In a further aspect, the present disclosure relates to a structure comprising an antimicrobial surface on a substrate, the antimicrobial surface comprising a plurality of nanoparticles having a width (Wh) of from 20 to 400 nm, packed in such a way that gaps exists in the surface, between nanoparticles, having a width (w), measured parallel to the substrate at at least one position along the height ($h_G$) of the gaps, of from 2 nm to 400 nm, such as from 2 to 40 nm, such as from 2 to 20 nm, such as from 2 to 10 nm and a depth (d) measured from the position to the substrate of at least 10 nm., the structure further comprising a coating layer covering the nanoparticles, the coating layer being thinner than the width of the particles or even thinner than half the width of the particles.

In embodiments, the area covered by the gaps, at the at least one position along the height ($h_G$), may represent at least 1% of the area of the structure at that height ($h_G$). For instance, it may represent from 1 to 50% and more typically from 1 to 15%, from 1 to 10% or from 1 to 8% of the area of the structure at that height (parallel to the substrate).

The characteristics of the structure, the surface, the substrate, the nanoparticles (called head in the first aspect), the gaps, and the coating can be as defined in any embodiment of the other aspects.

The invention will now be described by a detailed description of several embodiments. It is clear that other embodiments can be configured according to the knowledge of the person skilled in the art without departing from the true technical teaching of the invention, the invention being limited only by the terms of the appended claims.

EXAMPLE 1

Preparation of Different Nanostructured Si Surfaces

We now refer to FIG. 11. Several Si surfaces each comprising differently shaped nanopillars were prepared by lithography and plasma etching ($CH_2F_2/SF_6/N_2$ based chemistry) of Si wafers (14). This was performed by 1) providing a stack comprising a silicon substrate (14), an amorphous carbon hard mask (16) on the silicon substrate (14), an antireflective layer (17) on the hard mask (16), a positive photoresist (18) on the antireflective layer (17), 2) forming circular patterns (19) in the photoresist by immersion lithography (193 nm), the circular patterns (19) having the dimensions of the cross-section of the desired nanopillars (5), 3)

transferring the circular pattern (19) into the silicon substrate (14) by dry plasma etching ($CH_2F_2/SF_6/N_2$ based chemistry), thereby forming the nanopillars (5). In some cases, round $SiO_2$ heads (6) were deposited on top of the nanopillars (5) by sputtering or chemical vapor deposition, thereby forming nanostructures (4) forming an antimicrobial surface (2). In the case shown in FIG. 5, 100 nm SiO2 was deposited on 590 nm high nanopillars by sputtering with a Pfeiffer Spider 630 sputter coater.

We now refer to FIG. 1. A first comparative sample ("50 nm Wavy") comprised an undulating surface of nanopillars having a height of about 50 nm.

Figure 2:
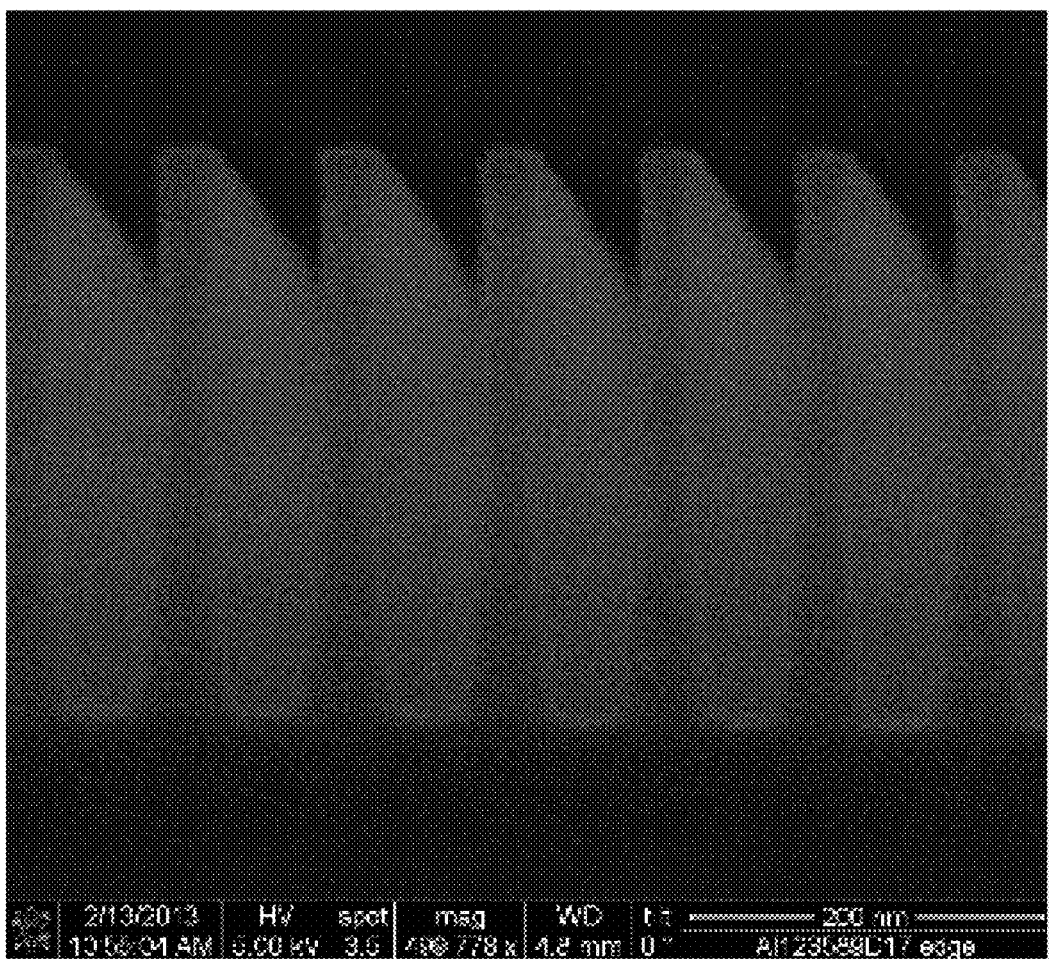
FIG. 2 illustrates a cross-sectional scanning electron image of different nanostructured surfaces according to comparative example, but which could be used as nanopillars to form nanostructures, according to example embodiments.

We now refer to FIG. 2. A second comparative sample ("330 nm") comprised nanopillars having a flat top and a height of about 330 nm.

Figure 3:
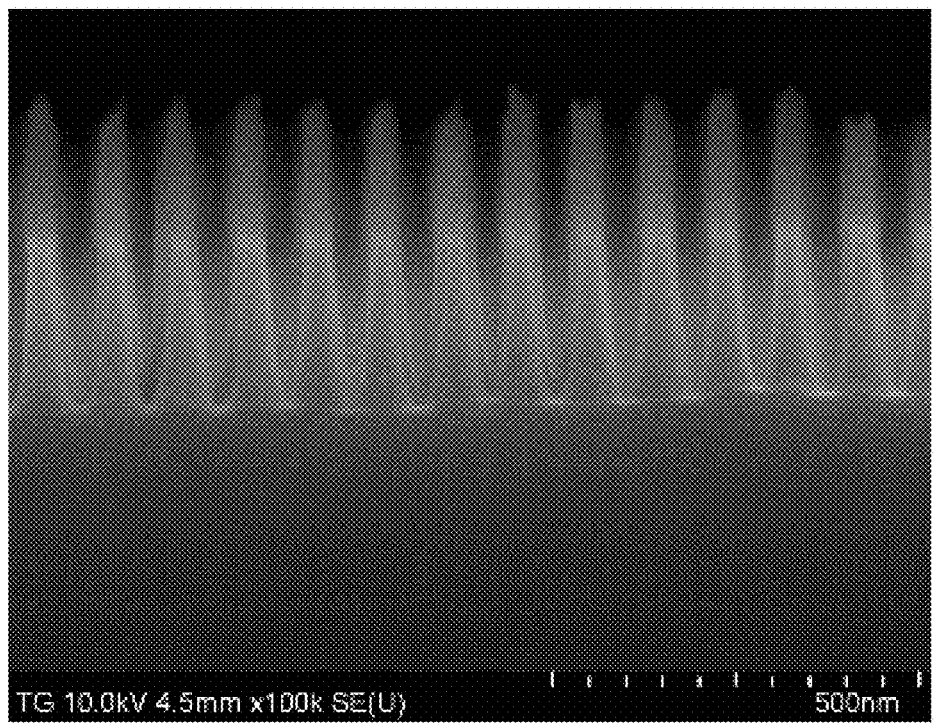
FIG. 3 illustrates a cross-sectional scanning electron image of different nanostructured surfaces according to comparative example, but which could be used as nanopillars to form nanostructures, according to example embodiments.

We now refer to FIG. 3. A third comparative sample ("350 nm with tips") comprised nanopillars having a sharp tip and a height of about 350 nm.

A fourth comparative sample ("420 nm"), which is not shown, comprised nanopillars having a flat top and a height of about 420 nm.

Figure 4:
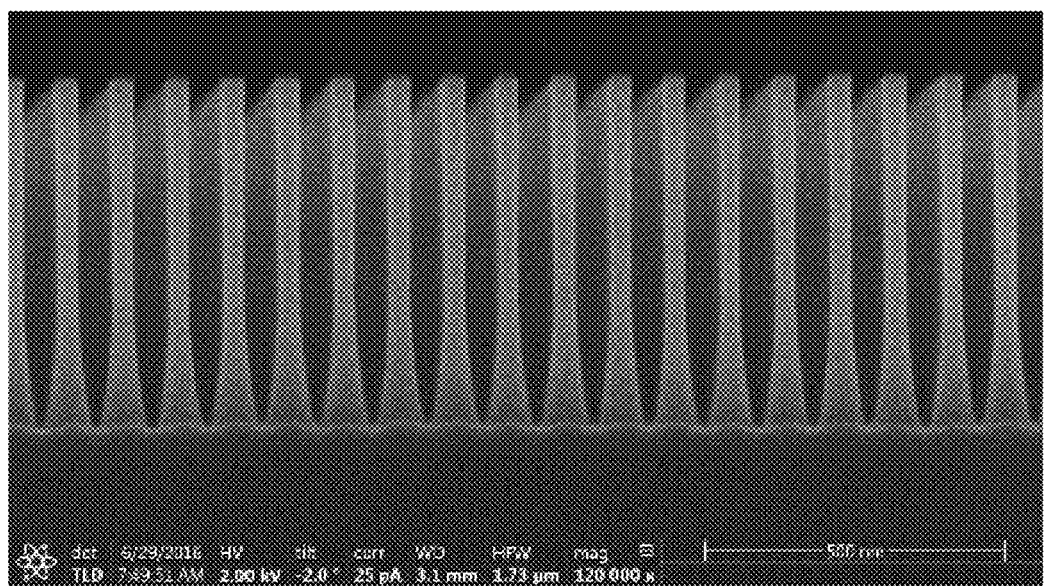
FIG. 4 illustrates a cross-sectional scanning electron image of different nanostructured surfaces according to comparative example, but which could be used as nanopillars to form nanostructures, according to example embodiments.

We now refer to FIG. 4. A fifth comparative sample ("580 nm") comprised nanopillars having a flat top and a height of about 580 nm.

Figure 5:
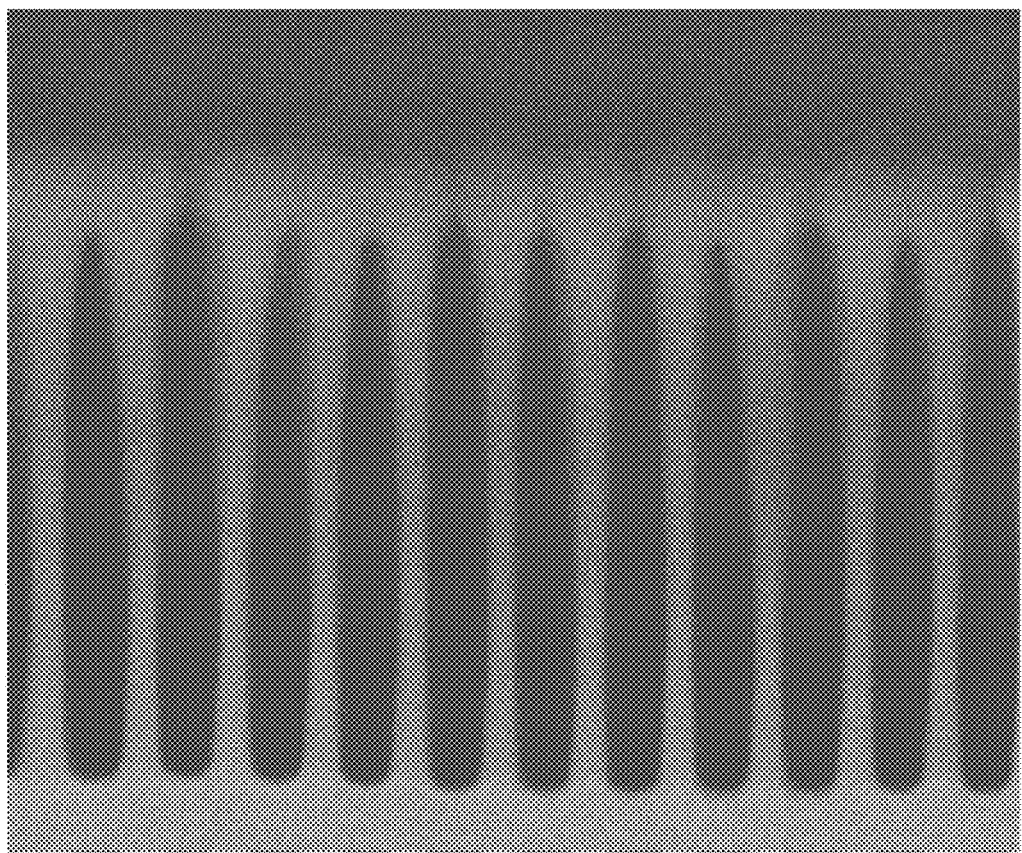
FIG. 5 illustrates a cross-sectional scanning electron image of a structure, according to example embodiments.

We now refer to FIG. 5. A sample according to an embodiment ("590 nm+100 nm Q-tip") comprised nanopillars having a round head of about 100 nm on top of a nanopillar having a height of about 590 nm.

We now refer to FIGS. 6A and 6B. A sixth comparative sample ("700 nm with tips") comprised nanopillars having a sharp tip and an irregular height up to about 700 nm. It is worth noting that each of these comparative samples could serve to make embodiments by adding a head on top of these nanopillars.

EXAMPLE 2

Comparison of the Different Nanostructured Surfaces

Preparation of Antibacterial Surfaces

Silicon and other (cf. infra) nanostructured surfaces were diced into surfaces of equal size (±0.8*0.8 mm) and cleaned with UV light and ozone. The cleaned surfaces were packed under low pressure pure nitrogen to prevent any molecules settling down on the clean surface during transport and temporary storage.

Preparation of the Initial Cell-suspension

*Escherichia coli* (BW25113, Keico wild-type) and mutants with the same genetic background were used in the experiment unless otherwise stated. Bacteria were grown overnight on 37° C. on an LB agar plate. From the overnight colonies, a small lob was taken and suspended in 1.5 ml MilliQ. This suspension was adjusted to $OD_{595}$ 0.3.

The cell suspension was diluted 200 times to obtain the final inoculum. The inoculum had an approximated concentration in the order of $10^6$ CFU/ml.

Incubation of the Surfaces

Freshly cleaned surfaces according to the present disclosure (as shown in FIG. 5) were carefully put into a sterile 24-well plate (Cellstar, Greiner Bio-One) using sterilized tweezers as to not scratch and thus damage the nanoimprinted surfaces. The inoculum was gently vortexed and 40 µl was put on each surface. 40 µl formed a thin film which covered the entire surface. Hydrophobic surfaces would not have a film on it, as the inoculum formed a droplet on the surface, occupying a surface area dependent on the contact angle of the inoculum on the coating. One or more empty wells were filled with 800 µl LB as a sterility control. The wells were covered with sterile Breathseal Sealers (Greiner Bio-One) and the lid, after which the well plate was carefully put in a humid controlled environment to prevent evaporation as much as possible. The surfaces were incubated on 37° C. for the desired incubation time. The initial inoculum was incubated on 37° C. in a separate Eppendorf tube for the same incubation time.

Plating and Counting

Once the desired incubation time had passed, 780 µl MilliQ was added to each well containing a surface. By pipetting up and down, the inoculum in the well was homogenized and the surface was washed. 200 µl was taken from the well and diluted in 800 µl MilliQ to make a $10^{-2}$ dilution of the inoculum. The plating was done via a standard plate count. The dilution of the inoculum was plated at least twice on agar plates containing either 1% or 0% NaCl, depending on the experiment. The plates were incubated at 37° C. for 18-24 h. The incubated initial inoculum was also plated at each time point. The viable cells were then counted.

Efficiency Calculation of Surfaces

To calculate the efficiency of the surfaces, the viable cell count of the incubated initial inoculum at that time point was averaged over the different platings. This count was subtracted by the viable cell count of the surfaces and divided by the averaged viable cell count of the incubated initial inoculum of that time point. This resulted in the fraction of killed cells by which the surfaces were benchmarked.

Figure 8:
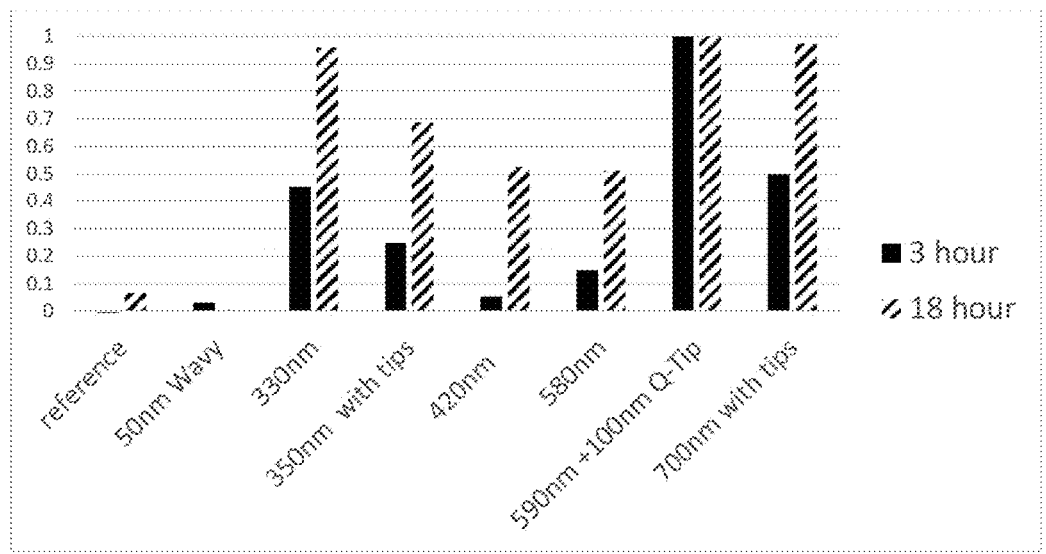
FIG. 8 illustrates a bar graph of the *E. coli* killing efficiency of different nanostructured surfaces according to comparative examples and according to example embodiments.

We now refer to FIG. 8. The killing efficiency of *E. coli* for the different nanostructured Si surfaces of example 1 and the reference is shown after 3 hours and 18 hours. Other than for the undulating surface ("50 nm wavy"), a considerable killing efficiency after 18 hours is found for all nanostructured Si surfaces. Nevertheless, the nanostructured surface of the present disclosure ("590 nm+100 nm Q-tip"), comprising both pillars and heads, vastly exceeded the other surfaces by reaching 100% efficiency and this already after 3 hours.

EXAMPLE 3

Preparation and Comparison of Nanostructured Surfaces Covered by an Antimicrobial Substance Si surfaces each comprising nanopillars were prepared as in example 1, the nanopillars having a flat top and a height of about 580 nm. A 5 nm or 10 nm $HfO_x$ layer was deposited on top of the nanopillars using atomic layer deposition. $HfO_x$ is known to be toxic to the *E. coli* bacteria.

Figure 9:
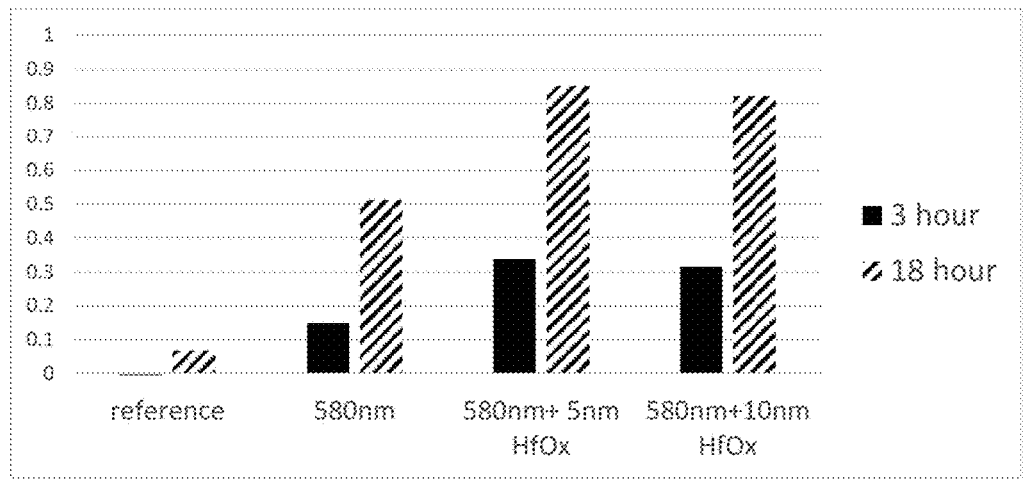
FIG. 9 illustrates a bar graph of the *E. coli* killing efficiency of different nanostructured surfaces according to comparative example.

We now refer to FIG. 9. The killing efficiency of *E. coli* for the fifth sample of example 1 ("580 nm"), the two present samples ("580 nm+5 nm HfOx" and "580 nm+10 nm HfOx") and the reference is shown after 3 hours and 18 hours. It was observed that coating the nanopillars in the toxic substance further increased their efficiency, with an increase in efficiency after 18 hours from about 50% to over 80%.

EXAMPLE 4

Preparation and Comparison of Nanostructured Surfaces Based on Block Copolymers

We now refer to FIG. 14. A polystyrene-block-poly (methyl methacrylate) (PS-b-PMMA) block copolymer layer (11) was phase separated into a PS cylindrical phase (12) and a PMMA phase, and the PMMA non-cylindrical phase was removed, leaving cylindrical PS nanopillars (5) on a substrate (3), the nanopillars (5) having a height of about 40 nm and a width of about 20 to 25 nm (see FIG. 7A).

In a further sample, the same procedure was repeated but the PS cylindrical domain was infiltrated with $AlO_x$ using a sequential infiltration synthesis and both polymer blocks were removed. This left $AlO_x$ nanopillars on a substrate, the nanopillars having a height of about 120 nm and a width of about 20 nm (see FIG. 7B) $AlO_x$ is also known to be toxic to *E. coli*.

Figure 10:
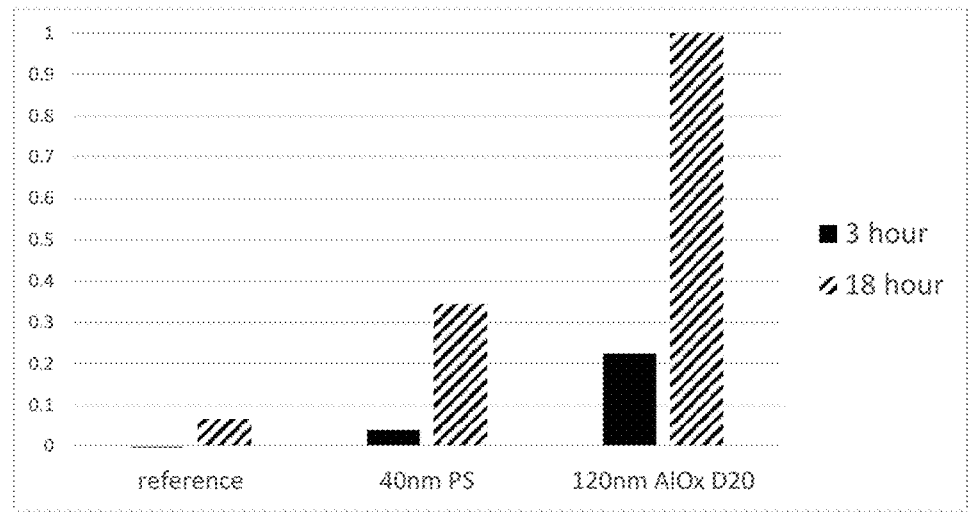
FIG. 10 illustrates a bar graph of the *E. coli* killing efficiency of different nanostructured surfaces according to comparative examples.

We now refer to FIG. 10. The killing efficiency of *E. coli* for the PS nanopillared surface ("40 nm PS"), the $AlO_x$ nanopillared surface ("120 nm AlOx D20") and the reference is shown after 3 hours and 18 hours. It was observed that these alternative nanostructured surfaces, i.e. based on organic materials, can also be effective. For the PS nanopillared surface a moderate killing efficiency is found, which is nevertheless fairly substantial when compared to the undulating surface of example 1 having a similar height ("50 nm Wavy"). For the $AlO_x$ nanopillared surface, comprising the toxic $AlO_x$, an efficiency of 100% is found after 18 hours.

EXAMPLE 5

Preparation of Seven Further Nanostructured Si Surfaces

Figure 15A:
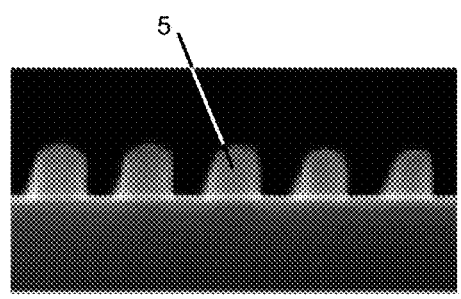
FIG. 15A illustrates a cross-sectional scanning electron image of a surface that includes a plurality of nanopillars as an intermediate to a structure, according to example embodiments.
Figure 15B:
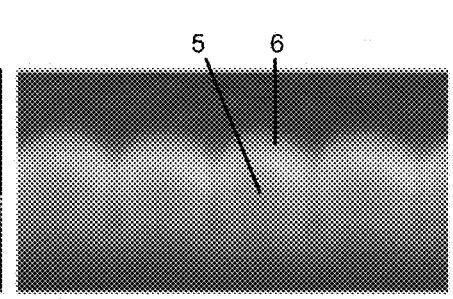
FIG. 15B illustrates a cross-sectional scanning electron image of the structures of FIG. 15A after the performance of step b1 of a method, according to example embodiments.

Different further nanostructured surfaces have been prepared by procedures analogous to example 1. All of these nanostructured surfaces comprised a square matrix of regularly spaced nanopillars. The center to center distance between nanopillars along a row or a column of the matrix was 90 nm. Each nanopillar had a regular width of 35 nm. Three of these surfaces comprised nanopillars but no heads. Surface no 1 had nanopillars that were 50 nm high (see FIG. 15A and FIG. 18A), Surface no 2 had nanopillars that were 330 nm high (see FIG. 16A) and surface no 3 had nanopillars that were 700 nm high. Four others of these surfaces comprised nanopillars on which a $SiO_2$ head had been sputtered. Surface no 4 had nanopillars that were 50 nm high and had a 90 nm thick $SiO_2$ layer sputtered thereon, thereby forming a hemispherical head covering the top of the nanopillars and their entire height (see FIG. 18B). Surface no 5 had nanopillars that were 50 nm high and had a 130 nm thick $SiO_2$ layer sputtered thereon (see FIG. 15B, FIG. 18C, and FIG. 21), thereby forming a square shaped head covering the top of the nanopillars and their entire height. The space between the heads was smaller than in the case of the hemispherical heads. Surface no 6 (see FIG. 16B) had nanopillars that were 330 nm high (with a flat top) and heads that covered only part of the height of the nanopillars and a Surface no 7 had nanopillars that were 700 nm (with a flat top) high and heads that covered only part of the height of the nanopillars.

Figure 20:
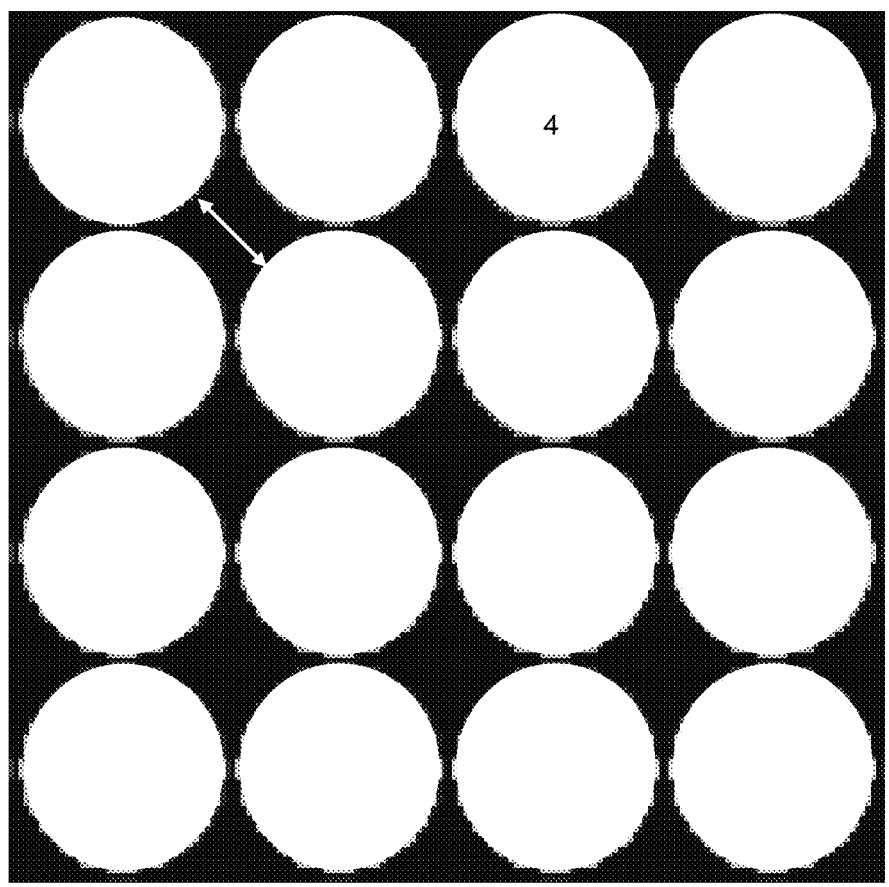
FIG. 20 schematically illustrates a top view of a structure, according to example embodiments.

FIG. 20 schematized a top view of an antimicrobial surface comprising a plurality of nanostructures (4). Such a top view represents schematically the situation of Surfaces no 4, 6, and 7. The double arrow shows a gap existing between two adjacent nanostructures. Due to the close-packing, such a gap in small enough to impart antimicrobial activity to the surface.

Figure 21:
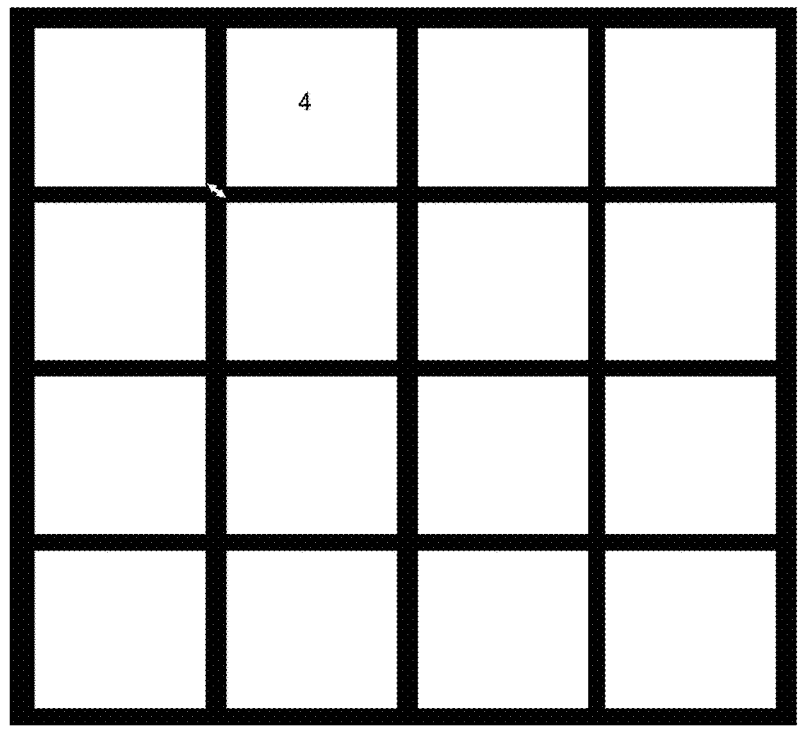
FIG. 21 schematically illustrates a top view of a structure, according to example embodiments.

FIG. 21 schematized a top view of an antimicrobial surface comprising a plurality of nanostructures (4). Such a top view represents schematically the situation of Surface no 5. The double arrow shows a gap existing between two adjacent nanostructures. Due to the close-packing and the thicker $SiO_2$ layer deposited on the nanopillars, such a gap in smaller than when a thinner SiO2 layer is deposited (situation of Surface no 4). This imparts to surface no 5 enhanced antimicrobial activity to the surface compared to Surface no 4.

EXAMPLE 6

Comparison of the Nanostructured Surfaces of Example 5 with Nanostructures Obtained in Example 1

The microbial surfaces and the cell suspensions were prepared as in example 2. Incubating of the surfaces, plating, counting, and efficiency calculations were also performed as in example 2. In addition to *E. coli*, *S. aureus* and mutants with the same genetic background have also been tested with similar results (not depicted in the figures).

We now refer to FIG. 17. The killing efficiency of *E. coli* for Surfaces 1 to 7, for the reference, and the reference coated with 100 nm $SiO_2$ (reference+SiOx), The killing efficiency for each surface are shown after 3 hours and 18 hours in contact with the bacteria. It can be observed that other than for the reference, the reference coated with $SiO_2$ (reference+SiOx), and surface 1 (50 nm), a considerable killing efficiency after 18 hours is found for Surfaces 2-7. Nevertheless, the nanostructured surface of the present disclosure (Surfaces 4-7) comprising a head, vastly exceeded the other surfaces by reaching 100% efficiency and this already after 3 hours.

EXAMPLE 7

Varying the Amount of $SiO_2$ Sputtered on Surface 1 or Example 5

Further experiments were performed by following the procedures of examples 5 and 6 where the amount of $SiO_2$ sputtered on Surface 1 or Example 5 was varied.

It was observed that for a thickness of $SiO_2$ deposition of from 85 nm to 130 nm, the surface became most effective in killing bacteria. A thickness in this range correspond to FIG. 15B and FIG. 18C where the distance between the heads is reduced to a minimum but leaving gaps between the heads. The heads exhibited a relatively square shape.

EXAMPLE 8

Formation of Antimicrobial Surfaces by Close-Packing Nanoparticles

We now refer to FIG. 19. Polystyrene particles (4) with a 499±5 nm diameter, purchased from Duke Scientific (Palo Alto, Calif.), are deposited on a PDMS substrate treated with an oxygen plasma by convective assembly, as disclosed in L. Malaquin et al. (Langmuir 2007, 23, 11513-11521), thereby obtaining a closely packed assembly of particles. These particles are then fixed to the substrate by either thermal bonding (top) or by applying a coating (20) on the particles (bottom).

This is repeated with 60 nm and 100 nm diameter polystyrene spheres purchased from Sigma-Aldrich.

This is repeated with $SiO_2$ nanospheres of sizes 50, 80, 100, 120, and 140 nm purchased from Sigma-Aldrich.

This is repeated with $Si_3N_4$ spherical particles of sizes 50, 1000, and 10000 nm purchased from Sigma-Aldrich.

This is repeated with iron oxide nanoparticles with a diameter in the range 50-100 nm purchased from Sigma-Aldrich.

EXAMPLE 9

Testing of the Antimicrobial Properties of the Samples of Example 8

Example 2 is repeated on the antimicrobial surfaces obtained in example 8.

It is to be understood that although example embodiments, specific constructions and configurations, as well as materials, have been discussed herein for devices according to the present disclosure, various changes or modifications in form and detail may be made without departing from the scope and technical teachings of the disclosure. For example, any formulas given above are merely representative of procedures that may be used. Functionality may be added or deleted from the block diagrams and operations may be interchanged among functional blocks. Steps may be added or deleted to methods described within the scope of the present disclosure.

What is claimed is:

1. A structure comprising an antimicrobial surface on a substrate, wherein the antimicrobial surface comprises a plurality of nanostructures, and wherein each nanostructure comprises:
   a nanopillar on the substrate, wherein the nanopillar has a height; and
   a head covering a distal end and at least part of the height of the nanopillar;
       wherein each of the heads covers only a part of the height of the respective nanopillar, thereby forming a nanopillar portion not covered by the head,
       wherein the nanopillar portions not covered by the heads have an average width,
       wherein the heads have a width and a height,
       wherein the widths of the heads are larger than the average width of the nanopillar portions not covered by the heads, and
       wherein the ratio of head width to head height is from about 0.7 to about 1.3.

2. The structure according to claim 1, wherein the head is round, spherical, spheroidal, ellipsoidal, or rectangular.

3. The structure according to claim 1, wherein the antimicrobial surface is synthetic.

4. The structure according to claim 1,
   wherein the antimicrobial surface comprises an antimicrobial property, and
   wherein the antimicrobial property of the antimicrobial surface is biophysical in nature.

5. The structure according to claim 1, wherein distances between corresponding points of two adjacent nanopillars of two adjacent nanostructures of the plurality of nanostructures is, on average, between 20 nm and 500 nm.

6. The structure according to claim 1, wherein an average width among the nanopillars of the plurality of nanostructures is between 10 nm and 300 nm.

7. The structure according to claim 1, wherein the height of each of the nanopillars is between 10 nm and 840 nm.

8. The structure according to claim 1,
   wherein the head has a width, and
   wherein the width of the head is between 40 nm and 510 nm.

9. The structure according to claim 1, wherein each of the nanopillar portions not covered by the heads are capable of flexing to an extent that heads of adjacent nanostructures within the plurality of nanostructures can touch each other.

10. The structure according to claim 1, wherein the structure is usable to kill or inhibit growth of a microorganism.

11. The structure according to claim 10, wherein the microorganism is a bacterium, a virus, or a fungus.

12. The structure according to claim 10,
   wherein the antimicrobial surface comprises gaps defined between the heads of adjacent nanostructures,
   wherein the gaps each have a width, measured parallel to the substrate at least one position along a height of the gaps, of between 2 nm and 40 nm, and
   wherein the gaps each have a depth measured from the at least one position along the height of the gaps to the substrate of at least 10 nm.

13. The structure according to claim 1,
   wherein the heads of the nanostructures are nanoparticles,
   wherein the nanoparticles have a width of between 20 nm and 400 nm,
   wherein the nanoparticles are packed in such a way that gaps exist in the antimicrobial surface, between the nanoparticles,
   wherein the gaps are between 2 nm and 400 nm,
   wherein the structure further comprises a coating layer covering the nanoparticles, and
   wherein the coating layer is thinner than the width of the nanoparticles.

14. The structure according to claim 13, wherein the coating layer is thinner than half of the width of the nanoparticles.

15. A method for making a structure comprising an antimicrobial surface on a substrate, comprising:
   providing a substrate with a plurality of nanopillars thereon, wherein each nanopillar has a height; and
   forming a head at a distal end of each nanopillar, wherein each head covers the distal end and at least part of the height of the respective nanopillar on which it is formed,
       wherein each of the heads covers only a part of the height of the respective nanopillar, thereby forming a nanopillar portion not covered by the head,
       wherein the nanopillar portions not covered by the heads have an average width,
       wherein the heads have a width and a height,
       wherein the widths of the heads are larger than the average width of the nanopillar portions not covered by the heads, and
       wherein the ratio of head width to head height is from about 0.7 to about 1.3.

16. The method according to claim 15,
   wherein each head only covers part of the height of the respective nanopillar on which it is formed, thereby defining a respective nanopillar portion that is not covered by the head, and
   wherein each head has a width that is larger than an average width of the respective nanopillar portion.

17. The method according to claim 15, wherein providing the substrate with the plurality of nanopillars thereon comprises:
   phase separating a layer of a block copolymer into a cylindrical phase and a non-cylindrical phase; and
   removing the non-cylindrical phase, thereby forming the plurality of nanopillars.

18. A method for making a structure comprising an antimicrobial surface on a substrate, comprising:

providing a mold for a plurality of nanostructures, comprising:
- a substrate-shaped cavity; and
- a plurality of nanostructure-shaped cavities opening therein, wherein each nanostructure-shaped cavity comprises:
  - a nanopillar-shaped portion; and
  - a head portion on a distal end of the nanopillar-shaped portion,
    - wherein the head portion has a width and a height, and the nanopillar portion has an average width,
    - wherein the width of the head portion is larger than the average width of the nanopillar portion, and
    - wherein the ratio of head width to head height is from about 0.7 to about 1.3;

filling the mold with a precursor material; and removing the mold from the precursor material.

19. The method according to claim 18, further comprising hardening the precursor material prior to removing the mold from the precursor material.

\* \* \* \* \*